(12) United States Patent
Delehanty et al.

(10) Patent No.: US 9,040,250 B2
(45) Date of Patent: May 26, 2015

(54) BINDING INTERACTION OF PROANTHOCYANIDINS WITH BACTERIA AND BACTERIAL COMPONENTS

(75) Inventors: James B Delehanty, Washington, DC (US); Brandy J White, Alexandria, VA (US); Baochuan Lin, Bethesda, MD (US); Frances S Ligler, Potomac, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1315 days.

(21) Appl. No.: 11/832,852

(22) Filed: Aug. 2, 2007

(65) Prior Publication Data

US 2008/0176933 A1 Jul. 24, 2008

Related U.S. Application Data

(60) Provisional application No. 60/824,794, filed on Sep. 7, 2006.

(51) Int. Cl.
| | | |
|---|---|---|
| G01N 33/554 | (2006.01) | |
| C07C 53/00 | (2006.01) | |
| C07H 21/00 | (2006.01) | |
| C12M 1/00 | (2006.01) | |
| C07K 14/00 | (2006.01) | |
| A61K 31/353 | (2006.01) | |
| C07D 311/62 | (2006.01) | |
| G01N 33/569 | (2006.01) | |

(52) U.S. Cl.
CPC ............ *A61K 31/353* (2013.01); *C07D 311/62* (2013.01); *G01N 2333/415* (2013.01); *G01N 2400/50* (2013.01); *G01N 33/56911* (2013.01)

(58) Field of Classification Search
CPC ............... A61K 31/353; C07D 311/62; G01N 2333/415; G01N 2400/50; G01N 33/56911
USPC ............................................... 514/456
See application file for complete search history.

(56) References Cited

U.S. PATENT DOCUMENTS 5,484,591 A * 1/1996 Young ........................ 424/150.1
5,629,021 A 5/1997 Wright (Continued)

FOREIGN PATENT DOCUMENTS

| EP | 1676572 A1 | 7/2006 |
|---|---|---|
| WO | 9912541 A1 | 3/1999 |

OTHER PUBLICATIONS

Labarbe et al., Quantitative Fractionation of Grape Proanthocyanidins According to Their Degree of Polymerization, Journal of Agricultural and Food Chemistry, Jun. 1999 vol. 47 No. 7 pp. 2719-2723.*

(Continued)

*Primary Examiner* — Savitha Rao
(74) *Attorney, Agent, or Firm* — US Naval Research Laboratory; Joseph T. Grunkemeyer

(57) ABSTRACT

A composition having proanthocyanidin compounds having an average degree of polymerization of at least about 6. A method of administering to an immunosuppressed patient or a patient diagnosed with sepsis or septic shock a composition having a proanthocyanidin. A method of administering to a patient diagnosed with a gram negative bacterial infection a composition having proanthocyanidin compounds having an average degree of polymerization of at least about 6.

10 Claims, 9 Drawing Sheets

(56) References Cited

U.S. PATENT DOCUMENTS

| | | | |
|---|---|---|---|
| 5,646,178 | A | 7/1997 | Walker et al. |
| 5,650,432 | A | 7/1997 | Walker et al. |
| 6,210,681 | B1 | 4/2001 | Walker et al. |
| 6,297,273 | B1 * | 10/2001 | Romanczyk, Jr. ............ 514/456 |
| 6,440,471 | B2 | 8/2002 | Walker et al. |
| 6,608,102 | B1 | 8/2003 | Howell et al. |
| 6,720,353 | B2 | 4/2004 | Howell et al. |
| 2001/0021398 | A1 | 9/2001 | Walker et al. |
| 2002/0028260 | A1 | 3/2002 | Walker et al. |
| 2003/0017998 | A1 | 1/2003 | Snow et al. |
| 2004/0142048 | A1 * | 7/2004 | Morre et al. ................ 424/729 |
| 2004/0156925 | A1 | 8/2004 | Howell et al. |
| 2004/0234480 | A1 | 11/2004 | Pauly et al. |
| 2005/0118239 | A1 | 6/2005 | Sabesan |
| 2007/0166409 | A1 * | 7/2007 | Royds ......................... 424/732 |

OTHER PUBLICATIONS

A.B. Howell et al. / Phytochemistry 66 (2005) 2281-2291.*
Le Roux et al., A-Type Proanthocyanidins from Pericarp of *Litchi chinensis*, Phytochemistry, vol. 48, No. 7 pp. 1251-1258, 1998.*
Dauer et al., Polymeric Proanthocyanidins from the Bark of *Hamamelis virginiana*, Planta Med. 2003; vol. 69, pp. 89-91.*
The Washington Manual of Medical Therapeutics, 31st edition, 2004, Lippincott Williams and Wilkins, pp. 294-295.*
http://medical-dictionary.thefreedictionary.com/sepsis accessed Sep. 2, 2010.*
Uthman (Bacterial sepsis, Mar. 31, 2004, downloaded from the Internet on Apr. 14, 2011, URL: http://replay.waybackmachine.org/20040331050253/http://web2.airmail.net/uthman/pdf_documents/sepsis.pdf.*
Bulega et al. (Journal of Science of Food and Agriculture, 80, 2000 pp. 1094-1117.*
Gu et al. (The Journal of Nutrition, 2004, pp. 613-617.*
Ahuja et al., *J. Urol.*, 159:559-562 (1998).
Allison et al., *J. Basic Microbiol.* 40:3-6 (2000).
Bodet et al., *Eur. J. Oral Sci.* 115:64-70 (2007).
Howell et al., *Phytochem.*, 66:2281-2291 (2005).
Bodet et al., *J. Dent. Res.* 85:235-239 (2006).
Bodet et al., *J. Periodont. Res.* 42:159-168 (2007).
Foo et al., *Phytochemistry* 54:173-181 (2000).
Howell et al., *N. Engl. J. Med.*, 339:1085-1086 (1998).
Johnson-White et al., *Anal. Chem.*, 78:853-857 (2006).
Liu et al., *Biotechnol. Bioeng.*, 93:297-305 (2006).
Raz et al., *Clin. Infect. Dis.*, 38:1413-1419 (2004).
Steinberg et al., *J. Antimicrob. Chemother.*, 54:86-89 (2004).
Steinberg et al., *Int. J. Antimicrob. Agents*, 25:247-251 (2005).
Zafriri et al., *Antimicrob. Agents Chemother.* 33:92-98 (1989).
Sen et al., "Regulation of inducible adhesion molecule expression in human endothelial cells by grape seed proanthocyanidin extract" Mol. Cell. Biochem., 216, 1-7 (2001).
Search report in EP07842034.6 (Feb. 10, 2010).
Muroi et al., "Structural Regions of MD-2 That Determine the Agonist-Antagonist Activity of Lipid IVa" J. Biol. Chem., 281, 5484-5491 (Mar. 3, 2006).
Jia et al., Natural Products: Drug Discovery and Theraputic Medicine, Humana Press (2005) Chapter 10: Challenges and Opportunities in the Chinese Herbal Drug Industry, pp. 229-250.
Office Action in U.S. Appl. No. 11/832,834 (Jul. 21, 2010).
Communication in EP07842034.6 (Aug. 13, 2010).
Office Action in U.S. Appl. No. 11/832,834 (Apr. 18, 2011).
Office Action in U.S. Appl. No. 11/832,834 (Oct. 14, 2011).

* cited by examiner

BINDING INTERACTION OF PROANTHOCYANIDINS WITH BACTERIA AND BACTERIAL COMPONENTS

This application claims the benefit of US Provisional Patent Application No. 60/824,794, filed on Sep. 7, 2006, incorporated herein by reference. U.S. patent application Ser. No. 11/832,834 is incorporated herein by reference.

FIELD OF THE INVENTION

The invention is generally related to proanthocyanidins.

DESCRIPTION OF RELATED ART

Polyphenolic compounds are widely distributed in higher plants and constitute a part of the human diet. Interest in polyphenolic compounds has been spurred by their potential health benefits arising from their antioxidant activity (Croft, Ann. NY Acad. Sci., 854, 435 (1998); Bravo, Nutri. Rev., 56, 317 (1998). All referenced publications and patent documents are incorporated herein by reference). The antioxidant activity of flavanoids has been studied in great detail (Rice-Evans et al., Free Rad. Biol. Med., 20, 933 (1996); Cos et al., Planta Med., 67, 515 (2001); Cos et al., J. Nat. Prod., 61, 76 (1998); Cos et al., In Studies in Natural Products Chemistry, Atta-ur-Rahrman, Ed., Elsevier Science B.V., Amsterdam (2000)). Tannins are an important group of polyphenolic compounds that are classified into three main groups: 1) the hydrolysable, 2) the complex, and 3) the condensed tannins or proanthocyanidins (PACs). PACs are high molecular weight polymers composed chiefly of the monomeric flavan subunits (+)-catechin and (−)-epicatechin and their derivatives whose structures consist of three phenyl rings each bearing various hydroxyl substituents (FIG. 1). PACs classified as "type-B" are characterized by single linked flavanyl units while "type-A" PACs contain an additional ether linkage between flavanyl subunits. Typical plant sources of PACs include fruits, leaves, and bark. In addition to their antioxidant activity, PACs have been shown to possess a number of other beneficial health effects including anti-cancer activity (Zhao et al., Carcinogenesis, 20, 1737 (1999); Bomser et al., Chem.-Biol. Interact., 127, 45 (2000)), anti-inflammatory activity (Yang et al., J. Nutr., 128, 2334 (1998); Sen et al., Mol. Cell. Biochem., 216, 1 (2001)), and cardioprotective properties (Reed, Crit. Rev. Food Sci., 42S, 301 (2002)). Recently, significant attention has been placed on the health effects of PACs from green tea (Dufresne et al., J. Nutr. Biochem., 12, 404 (2001)), grapes (wines, juices, and grape seed extracts) (Bagchi et al., Mut. Res., 523, 87 (2000)), and cranberry juice (Foo et al., Phytochemistry, 66, 2281 (2000)). Specifically, PACs from the American cranberry (Vaccinium macrocarpon) are well documented in their ability to protect the urinary tract against the adherence of uropathogenic bacteria and drinking cranberry juice is a recommended treatment for various urinary tract infections and prostatitis. It has been shown that cranberry PACs inhibit the adherence of P-fimbriated Escherichia coli to cellular surfaces bearing α-Gal (1→4) β-Gal receptor sequences similar to those on epithelial cells of the urinary tract (Foo). This effect is mediated largely via A-type PAC-induced conformational changes within the fimbriae proteins which undermine their ability to interact with cell surface receptors on uroepithelial cells (Howell et al., Phytochemistry, 66, 2281 (2005)). More recently, it has been shown that cranberry juice effectively reduces the adhesive forces between P-fimbriated E. coli and a silicon nitride probe surface (Liu et al., Biotech. Bioeng., 93, 297 (2006)).

Current strategies for filtering and/or concentrating bacteria and bacterial components are most often aimed at removing the materials from solutions through such non-selective means as size exclusion and electrostatic interaction. Examples of sized exclusion-based and electrostatic-based filter devices are Costar Corp.'s cellulose acetate filters (size-based) with pore sizes of 0.22 µm to remove particles larger than the size cutoff and Argonide Corp.'s NANOCERAM® electropositive nanometer aluminum oxide fibers (surface charge-based) that nonspecifically bind materials bearing a net negative surface charge (e.g., bacteria and viruses). More specific filtration and concentration regimes utilize specific recognition elements (antibodies, peptides, aptamers, etc.) to specifically bind to molecules contained on or within the bacterial materials. Each of these technologies has its own inherent limitations. Size exclusion and charge-based filters require expensive manufacturing facilities and are often not re-usable once a certain binding capacity has been reached. Filters and concentrators based on specific recognition elements require the isolation of molecules with suitable binding characteristics followed by their large-scale preparation and purification.

Current therapeutic regimes for the neutralization and/or removal of bacteria and bacterial components from host organisms (e.g., humans and domestic livestock) are based largely on the use of antibiotics. Since their introduction in the 1940's, antibiotic drugs have proven effective for the treatment of many bacteria-related illnesses. However, their frequent misuse has given rise to antibiotic-resistant bacterial strains that have necessitated the development and implementation of increasingly more powerful drugs. Further, while antibiotics effectively inhibit bacterial replication, they are often ineffective at neutralizing harmful bacterial toxins. For example, lipopolysaccharide (LPS), the major component of the outer leaflet of the outer cell membrane of Gram-negative bacteria, is a major cause of complications during bacterial infection. LPS, commonly referred to as bacterial "endotoxin," is responsible for stimulating the body's normal inflammatory response against infection. Left unchecked, however, LPS hyperstimulation can result in a life-threatening hyperactivation of the inflammatory cascade known as systemic inflammatory response syndrome (sepsis).

LPS is a complex glycolipid that comprises the major portion of the outer leaflet of the outer membrane of Gram-negative bacteria (Reatz, Ann. Rev. Biochem., 59, 129-170 (1990)). It is composed of two main domains: 1) a lipid A core that is responsible for stimulating the immune system through its interaction with Toll-like receptor 4 (TLR-4) and 2) an elongated, branched polysaccharide tail. A potent immune response ensues upon the recognition of LPS by mammalian cells, including the production and release of cytokines, activation of complement, and various other effects that result in the killing and clearance of the pathogen. Uncontrolled hyperinflammatory host responses to LPS may lead to such life-threatening complications as septic shock, multiorgan failure, and even death. Polymyxin B (PB) is a cyclic cationic antibiotic decapeptide that has been demonstrated to be one of the most efficient compounds exhibiting LPS-binding and outer membrane-disorganizing capabilities (Danner et al., Antimicrob. Agents Chemoth., 33, 1428 (1989)). PB is believed to inhibit the biological activity of LPS via high-affinity binding to the lipid A moiety (Moore et al., Antimicrob. Agents Chemoth., 29, 496 (1986)).

In light of the costs and limitations associated with current technologies for the filtration and therapeutic neutralization of bacteria and bacterial components, inexpensive alternatives to achieve these same tasks would be advantageous.

SUMMARY OF THE INVENTION

The invention comprises composition comprising proanthocyanidin compounds, wherein the average degree of polymerization of all the proanthocyanidins in the composition is at least about 6.

The invention further comprises a method comprising: administering to an immunosuppressed patient or a patient diagnosed with sepsis or septic shock a composition comprising a proanthocyanidin.

The invention further comprises a method comprising: administering to a patient diagnosed with a gram negative bacterial infection a composition comprising a proanthocyanidin compound; wherein the average degree of polymerization of all the proanthocyanidins in the composition is at least about 6.

BRIEF DESCRIPTION OF THE DRAWINGS

A more complete appreciation of the invention will be readily obtained by reference to the following Description of the Example Embodiments and the accompanying drawings.

FIG. 4 shows that cranberry PACs slightly reduce membrane binding of LPS and significantly inhibit LPS endocytosis. HEK 293 cells stably expressing CD14 and TLR4/MD2 were incubated with 25 nM LPS and 0.5 µM cranberry PAC for 1.5 h. Cells were either fixed (A) or fixed and permeabilized (B) and incubated with a goat anti-LPS antibody conjugated to fluorescein to visualize LPS. Where indicated, LPS binding was functionally blocked by co-incubation with lipid A or anti-TLR4 and anti-CD14 antibodies. (A) PACs slightly inhibit the binding of LPS to the cell surface. (B) PACs significantly abrogate endocytosis of LPS. The arrows indicate regions of internalized LPS. Nuclei are stained with DAPI. Quantitative analysis of LPS membrane binding and LPS endocytosis are shown in (C) and (D), respectively. Symbols correspond to levels of significance relative to control (determined by Student's t-test): (*) $p<0.1$, (♦) $p<0.05$, (§) $p<0.01$, (¤) $P<0.001$.

μg/mL and capture molecule concentration was 5.5 μM for PACs from tea (solid circles) and 6.0 μM for PACs from cranberries (open squares).

Figure 12:
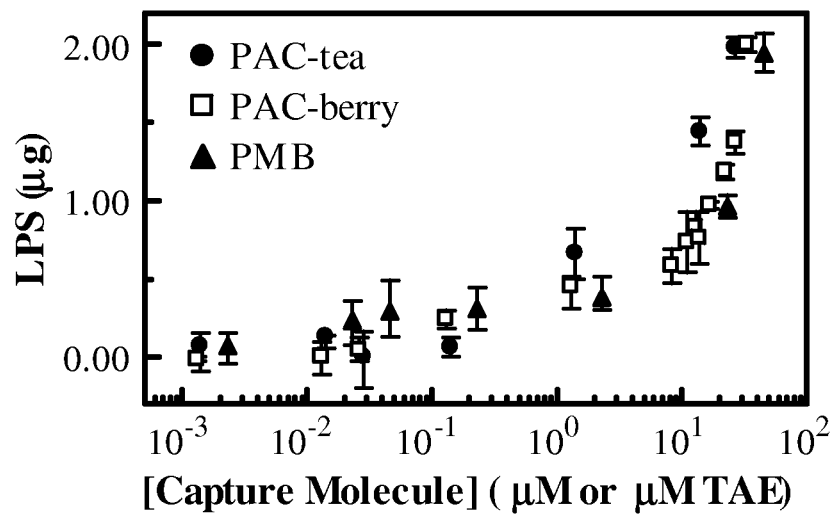

FIG. 12 presents a comparison of proanthocyanidin capture of LPS to that of polymyxin B. Immobilized PMB (solid triangles) and PACs from tea (solid circles) and cranberries (open squares) show similar binding affinities for FITC-LPS when compared in side-by-side assays. FITC-LPS concentration was 145 μg/mL.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Grape seeds (Vitis vinifera) and white pine (Pinus maritima) are sources of proanthocyanidins, but the compounds are also found in food items such as teas, coffees, chocolate, apples, berries, and barley, to name a few. PACs are found in heterogeneous mixtures consisting of various numbers of monomer subunits. Catechin and epicatechin are the most common of the subunits. Intersubunit linkages are usually via single intermolecular bonds between carbon atoms, but in some species subunits are linked by two intermolecular bonds: one carbon-carbon and one carbon-oxygen (FIG. 2) (Yoshida et al., *J. Syn. Org. Chem. Jpn.*, 62, 500 (2004); Foo et al., *Phytochemistry*, 54, 173 (2000)). These are referred to as B-type and A-type proanthocyanidins, respectively. Differing biological activities have been shown for A-type and B-type proanthocyanidins as well as for proanthocyanidins of differing subunit composition and differing degrees of polymerization (Kolodziej et al., *Phytother. Res.*, 9, 410 (1995); Howell et al., *Phytochemistry*, 66, 2281 (2005)).

PACs from cranberries, tea, and grapes may bind efficiently to LPS from various bacterial species. It is demonstrated that for cranberries, the most potent LPS-binding activity is contained within a PAC fraction composed of a mixture of polymers with an average degree of polymerization of twenty-one. While this fraction modestly inhibits the binding of LPS to the surface of HEK 293 cells expressing the full complement of LPS receptors (TLR4 (Toll-like receptor 4)/MD2 and CD14), it significantly abrogates the endocytosis of LPS. This PAC fraction also inhibits LPS-induced nuclear factor-κB activation in a manner that is not overcome by excess LPS. This effect is mediated through the inhibition of LPS interaction with TLR4/MD2 and the partial abrogation of LPS interaction with CD14. Importantly, PAC concentrations that mediate effective LPS neutralization elicit minimal in vitro cytotoxicity. The results demonstrate the potent LPS binding and neutralization properties of PACs and identify PACs as a new class of LPS antagonist with potential utility in endotoxin removal and the in vivo treatment of sepsis.

LPS present in blood binds to LPS-binding protein (Tobias et al., *J. Biol. Chem.* 264, 10867-10871 (1989)), which transfers LPS to the membrane-anchored receptor, CD14, on mononuclear macrophages. CD14 then mediates the interaction of LPS with the bipartite receptor complex, Toll-like receptor 4/MD2 (TLR4/MD2), resulting in intracellular signaling and production of nuclear factor-κB (NF-κB)-activated inflammatory cytokines (Shimazu et al., *J. Exp. Med.*, 189, 1777-1782 (1999)). These cytokines include tumor necrosis factor alpha (TNFα) and interleukins (IL-1α, IL-1β, and IL-6). Therapeutic strategies for sepsis, therefore, have been aimed at the neutralization of cytokines (Abraham et al., *J.A.M.A.* 273, 934-941 (1995)) or their receptors (Fisher et al., *J.A.M.A.* 271, 1836-1843 (1994)). Additional approaches have focused on the neutralization of LPS with cationic compounds (Andra et al., *J. Endotoxin Res.* 12, 261-277 (2006)) or lipid A-like substances (Lien et al., *J. Biol. Chem.* 276, 1873-1880 (2001); Visintin et al., *J. Immunol.*, 175, 6465-6472 (2005)). Unfortunately, clinical results for these strategic avenues remain disappointing.

Proanthocyanidins (PACs) are plant-derived polyphenolic compounds composed of flavanoid subunits and they have recently been associated with several potential positive health benefits. Detailed studies have attributed this activity to PACs with a degree of polymerization of 4 to 5 containing at least one unique interflavan subunit linkage consisting of one carbon-carbon and one carbon-oxygen bond (referred to as an A-type linkage) (Foo). More recently, it has been shown that PACs induce conformational changes in bacterial P-fimbriae proteins that reduce their adhesive forces for epithelial cell surface receptors (Liu). Recent work pointed to further interactions between high molecular weight polymers (average degree of polymerization of twenty-one) from cranberry juice which inhibited the nonspecific adhesion of bacteria to a protein-functionalized immunosensor surface (Johnson-White et al., *Anal. Chem.*, 78, 853-857 (2006)). Based on this evidence, the potential for previously undescribed interactions of cranberry juice components with the bacterial cell surface were investigated.

The LPS binding properties of PACs from cranberries, tea, and grapes are reported herein. Focusing more closely on PACs from cranberries, their ability to bind LPS from multiple bacterial species, primarily through interaction with the conserved lipid A moiety, is demonstrated. The PACs' ability to inhibit the interaction of LPS with cells expressing the full complement of LPS receptors was determined. PACs inhibit LPS interaction with mammalian cells largely through abrogation of LPS interaction with TLR4/MD2, an activity that also mediates the inhibition of LPS-induced NF-κB activation.

The interaction of PACs with bacterial cells for the prevention of bacterial cell adhesion to proteins is demonstrated on glass surfaces used in immunoassay techniques. Further demonstrated is a heretofore undescribed interaction of cranberry PACs with the bacterial cell surface component, lipopolysaccharide (LPS; also known as bacterial endotoxin). The interaction of cranberry PACs with the P-type fimbriae of *E. coli* has been described previously for the prevention of adhesion of bacterial cells expressing P-fimbriae to the cells of mammalian urinary and digestive tracts. The interaction of PACs with lipopolysaccharide has not been described previously. Based on this activity, PACs have potential uses in the filtration, concentration, and neutralization of bacterial endotoxins, bacterial cells, and bacterial cell components. Additionally, PACs may have uses in therapeutic applications where the neutralization and/or removal of bacteria and bacterial cell components are warranted.

PACs may offer a number of advantageous new features that make them suitable replacements or alternatives for current filtration, concentration, and neutralization applications. PACs are natural products that are produced by higher plants. Hence, a theoretically "unlimited" supply is afforded by nature. They do not require expensive manufacturing or machining facilities to produce as is the case with manufactured filtration and concentration devices. All that is required is the extraction and purification of the natural materials in order to harness their benefit.

For therapeutic applications, PACs may be an attractive alternative to the widespread use of antibiotics and current toxin-neutralizing compounds. For example, antibiotics are the most common treatment for urinary tract infections and antibiotic spending to treat these infections currently totals more than $1.6 billion annually. Given the mounting concern over the increase in antibiotic-resistant bacterial strains, alternative therapeutic measures that alleviate the dependence on antibiotics are being sought. The in vivo neutralization of bacterial toxins with compounds such as polymyxin B and its derivatives is currently the recommended course of treatment to mitigate the onset of immune hyperstimulation during bacterial infections. However, the inherent toxicity of such compounds has limited their use and has necessitated the development of less toxic derivatives that retain efficacy. The PAC materials described herein, with relative affinities comparable to those of polymyxin B, may offer suitable alternatives for toxin neutralization.

Interactions of PACs with P-fimbrae on cell surfaces are disclosed for the reduction of cellular adhesion. Other potential interactions of PACs with various cell surface components provide potential mechanisms for the neutralization of bacterial cells. Proteins such as cell surface protein antigen and glucosyltransferases are involved in colonization. Other proteins are involved in various signaling pathways and in quorum sensing. Sugars on a cell's surface are also involved in communication and anchoring and may serve as receptors. They are often the route through which pathogens such as viruses locate and interact with cells. The specific interaction between E. coli and PACs from cranberries not observed with PACs from other juices indicates specificity in the function of various PAC species and indicates the potential for a range of interactions with cellular surface components that have not yet been fully explored.

The PACs may be used in a composition, device, or component that may be useful in filtering, detecting, removing, or otherwise interacting with bacteria and/or LPS. In such a composition, the PAC is immobilized to a macromolecule, an assembly of macromolecules, a semi-solid, or a solid surface. The immobilized PAC may be exposed to a sample suspected of containing LPS, lipid A, or a bacterium that produces LPS or lipid A. In the case of macromolecules, the PAC may be immobilized to the macromolecule by covalent bonding or any other form of bonding or forces. The macromolecules or assembly of macromolecules may, for example, assist in transporting the PAC to a destination in an organism or be part of a sensor. Suitable macromolecules include, but are not limited to, macromolecules that comprise an amino acid, a peptide, a protein, a nucleotide, a nucleic acid, a lipid, or a carbohydrate. Suitable assemblies of macromolecules include, but are not limited to, those that comprise a multi-protein complex, a virus, a dendrimer, a nanoparticle, a nanocluster, a nanocrystal, a nanorod, a nanosphere, or a nanotube. Solid and semi-solid surfaces may be useful in, for example, sensor and filters. Semi-solids include materials such as hydrogels. Suitable solid or semi-solid surfaces include, but are not limited to, a plurality of beads, a sphere, a rod, fibers, filaments, capillaries, a tube, a planar layer, or a waveguide.

The degree of polymerization of the PAC may be selected depending on the particular application. Suitable average degrees of polymerization of all the PACs in a composition include, but are not limited to, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. The PAC may contain only catechin and epicatechin units or may contain other flavanoid units.

The PACs may be used in a filter apparatus. Such an apparatus may comprise a housing having an inlet and an outlet to allow fluid flow through the housing and the immobilized PAC. The immobilized PAC is maintained within the housing when fluid is flowed through the housing. This may be useful for removing bacteria and/or LPS from a fluid such as blood. An infected patient's blood may be passed through the filter and injected back into the patient. The filter may also be useful for decontamination and purification.

The PACs may be used in a sensor apparatus. Such an apparatus may comprise a fluid flow apparatus, the immobilized PAC, and a mechanism for detecting the binding of LPS, lipid A, or bacteria to the PAC. The mechanism may be any mechanism used in sensors for detection of a binding event, including but not limited to, an optical mechanism, ultraviolet light absorbance, visible light absorbance, infrared absorbance, fluorescence, luminescence, chemiluminescence, polarization, surface plasmon resonance, changes in refractive index, an acoustic mechanism, a surface acoustic wave device, a quartz crystal microbalance device, an electrochemical mechanism, or amperometric, potentiometric, or conductimetric measurements.

A filtering or sensing apparatus may be used with a variety of samples, including but not limited to, a clinical sample, blood, plasma, serum, lymph, spinal fluid, a pharmaceutical preparation (which may require decontamination) or a food or beverage intended for infants or immunosuppressed individuals.

Several example strategies for immobilization of PACs are described herein.

(1) Direct reactivity of PAC hydroxyls—The hydroxyls within PACs react similarly to amino groups toward acylating agents, compounds that contain an activated acyl group where the nucleophile attacks at the carbon displacing a leaving group. Acylating agents include, but are not limited to, the acid anhydrides, isocyanates, isothiocyanates, imidoesters, acid halides, N-hydroxysuccinimdyl and other activated esters. Thus, crosslinking agents bearing one of these acylating groups on one end (directed at the PAC hydroxyls) and another functional group (directed toward reactive groups on the targeted surface or macromolecule) are suitable for the immobilization of PACs. A number of such crosslinkers are available commercially (see, for example, www.piercenet.com). Three examples of direct reactivity are described below.

(1A) Immobilization of proanthocyanidins on sulfhydryl-bearing macromolecules. Purified PACs can be immobilized onto proteins or other sulfhydryl-bearing macromolecules and surfaces through the use of N-[p-maleimidophenyl] isocyanate (PMPI, Pierce). Incubation (45 min at room temperature) of PACs with PMPI at a molar ratio of 1:10 in 10 mM borate buffer at pH 8.5 results in reaction of the isocyanate group of PMPI with the hydroxyl groups of the PACs to produce carbamate linkages. Addition of the sulfhydryl-bearing compound and sodium phosphate buffer (pH 7, final concentration 50 mM) results in reaction of the maleimide group of PMPI with the sulfhydryl groups of the proteins or other macromolecules. The concentration of the macromolecule can be varied to influence the number of PACs bound to each molecule.

(1B) Immobilization of proanthocyanidins on amine-bearing macromolecules. Purified PACs can be immobilized onto proteins or other amine-bearing macromolecules and surfaces through the use of 4-(chlorosulfonyl) phenyl isocyanate (CSPI). Incubation (45 min at room temperature) of PACs with CSPI at equimolar concentrations in borate buffer at pH 8.5 results in reaction of the isocyanate groups of CSPI with the hydroxyl groups of the PACs to produce carbamate linkages. Addition of the amine-bearing macromolecule then allows the reaction of the chlorosulfate group of CSPI with surface amine groups to proceed, producing sulfonamines through the mechanism employed by the Hinsberg Test.

(1C) Immobilization of proanthocyanidins on amine or carboxyl-bearing macromolecules. Amine or carboxyl-bearing macromolecules can be modified through the use of 3-[(2-aminoethyl)dithio]propionic acid•HCl (AEDP) in the presence of 1-ethyl-3-[3-dimethylaminopropyl]carbodiimide hydrochloride (EDC). The use of a reducing agent such as tris[2-carboxyethyl]phosphine hydrochloride (TCEP) or 2-mercaptoethylamine cleaves the S—S bond of the AEDP producing a sulfhydryl group. A PMPI crosslinker can then be used to bind proanthocyanidins to this sulfhydryl group as described above (1A).

(2) Conversion of hydroxyls to alternative functional groups. (2A) Conversion of hydroxyls to aldehydes. The vicinal hydroxyl groups of PACs are susceptible to oxidation with periodic acid, sodium or potassium periodate. Periodate oxidation cleaves C—C bonds bearing adjacent hydroxyls, converting them to dialdehydes (Bobbit, *Adv. Carbohyd. Chem.*, 11, 1 (1956)). After periodate treatment, the dialdehyde formed can react with a variety of reagents, notably with amine groups to form imines of Schiff bases.

(2B) Conversion of hydroxyls to sulfhydryls. PAC hydroxyls can be converted into sulfhydryl groups. The hydroxyl group can be activated with tosyl chloride (toluenesulfonyl chloride) in phosphate buffer (pH 8 to 9) containing dioxane or pyridine. Subsequent trans-esterification is achieved in 0.5 M thioacetate solution at pH 5.5. Hydrolysis of the thioester to generate a free thiol is done with 0.5 N methanoate.

The properties described here show that PACs may be useful in treating patients diagnosed with a gram negative bacterial infection or sepsis or immunosuppressed patients. Any pharmaceutically acceptable treatment using a composition comprising a PAC may be used. The treatment may be more effective when performed in a combination therapy with an antibiotic, a chemotherapeutic, a radionucleide, an immunosuppressive drug, a plasmapheresis treatment. The PAC may also be conjugated to an antibiotic, a chemotherapeutic, a radionucleide, or an immunosuppressive drug.

One example application is binding of LPS, lipid A, or bacterial cells for their removal. The immobilization of PACs to any number of macromolecules, assembly of macromolecules, or surfaces would allow PACs to be used as recognition elements for the 1) removal, 2) concentration, and 3) purification of lipopolysaccharide, lipid A, or bacterial cells from solutions where their presence is not desired. This binding can take either of two forms: direct or indirect. The direct binding embodiment applies to instances in which the PACs are immobilized to solid and/or semi-solid surfaces (comprising beads, spheres, rods, fibers, filaments, capillaries, tubes, planar layers, or waveguides). Herein, the bead-immobilized PACs capture the target lipopolysaccharide, lipid A, or bacterial cells and the resulting complexes are centrifuged or magnetically concentrated such that the supernatant is easily removed, resulting in solid support-associated LPS, lipid A, or bacterial cells. Alternatively, PACs immobilized in this way can be used in a column format, wherein a packed column of PAC-functionalized support is exposed to a solution containing LPS, lipid A, or bacterial cells. Indirect embodiments involve the immobilization of PACs to macromolecules and assemblies of macromolecules. These are used to bind the LPS, lipid A, or bacterial cells in solution. After binding, addition of solid-support-immobilized recognition elements directed against the macromolecules or assemblies of macromolecules to which the PACs are attached allow for capture of the complexes and their removal from solution. In this scenario, the macromolecule used can be comprised of any of the following: an amino acid, a peptide, a protein, a nucleotide, a nucleic acid, a lipid, or a carbohydrate. The assemblies of macromolecules can be comprised of any of the following: a multiprotein complex, a virus, a dendrimer, or a nanoparticle. The nanoparticles can comprise a nanocluster, a nanocrystal, a nanorod, a nanosphere, or a nanotube.

Another example application is binding of LPS, lipid A, or bacterial cells for their detection. PACs' ability to bind LPS, lipid A, or bacterial cells can also be used to achieve the detection of LPS, lipid A, or bacterial cells once they are bound. Essentially, a sensor based on immobilized PACs comprises the immobilized PACs (as described above), a fluid flow apparatus, and a mechanism for achieving the detection of the bound LPS, lipid A, or bacterial cells. The detection can comprise the following methods: optical (UV or infrared absorbance, fluorescence, luminescence, chemiluminescence, polarization, surface plasmon resonance, changes in refractive index) acoustic (surface acoustic wave, quartz crystal microbalance), electrochemical (amperometric, potentiometric, conductimetric).

Another example application is binding of LPS, lipid A, or bacterial cells for therapeutic applications. The envisioned therapeutic applications of PACs are both in vivo and ex vivo. The in vivo applications comprise the administration of PACs (either passively through the diet or actively through bolus pill form or injection) to patients who are at risk of or are suspected to have a bacterial infection. The use of PACs in combination with other established antibacterial, antiviral, and antifungal methods is also envisioned. Such combination therapies comprise the simultaneous administration of PACs along with traditional antibiotic, antifungal, or antiviral medications. The direct immobilization (via the methods described above) of PACs to these types of medications The ex vivo applications comprise the use of PACs in a number of formats. These include the topical application of PACs to areas of the skin that are susceptible to bacterial infection. These also include use of PACs in plasmapheresis applications, wherein a patient's plasma is removed, incubated with PACs to remove LPS, lipid A, and bacterial cells and then the plasma is subsequently restored to the patient.

The presence of LPS during bacterial infection is a primary cause of sepsis, a severe inflammatory condition for which effective therapies remain limited. Among the more recent strategies for the neutralization of LPS are the use of natural and synthetic cationic compounds and lipid A-like substances. Cationic compounds, including peptides based on the binding domains of natural LPS-binding proteins and antimicrobial peptides, have exhibited affinities for LPS in the nanomolar range (Andra et al., *J. Endotoxin Res.*, 12, 261-277 (2006)). The cyclic nonapeptide polymyxin B, which binds to the lipid A moiety of LPS, has received considerable attention for its potent LPS neutralizing activity (David et al., *Biochim. Biophys. Acta.*, 1165, 147-152 (1992)). However, its clinical utility has been hampered by its considerable toxicity. Lipid A-like substances, which mimic the conserved lipid A moiety, function by preventing the interaction of LPS with its receptors. For example, E5564 is a second-generation synthetic lipodisaccharide designed to abrogate LPS interaction with the TLR4/MD2 receptor (Lien et al., *J. Biol. Chem.*, 276, 1873-1880 (2001); Visintin et al., *J.*

*Immunol.*, 175, 6465-6472 (2005)). Despite their potent LPS neutralizing activity, cationic compounds and lipid A-like substances are often limited by either their toxicity or their ability to be overcome by high LPS concentrations (Golenbock et al., *J. Biol. Chem.*, 266, 19490-19498 (1991)). LPS binding compounds that overcome these deficiencies are needed.

Described herein is a previously unreported biological activity of naturally-occurring plant PACs: the efficient binding and neutralization of bacterial LPS. The results demonstrate that PACs from cranberries, tea, and grapes bind LPS in a dose-dependent manner. Further, in the case of cranberry PACS, larger polymers (with an average degree of polymerization of twenty-one) exhibit the most potent LPS-binding activity.

Previous work has established the important role of PAC interaction with components of the bacterial cell surface. Foo et al. demonstrated that LH20-purified PACs from cranberries inhibited the adherence of P-fimbriated *E. coli* to surfaces containing $\alpha$-Gal(1$\rightarrow$4)$\beta$-Gal receptor sequences (Foo et al., *Phytochemistry*, 54, 173-181 (2000)). This activity was associated with PACs with a degree of polymerization of 4 to 5 and bearing at least one A-type linkage. Howell et al. later reported that this effect was, indeed, specific to A-type linkages, as B-type linked PACs from various sources did not mediate the effect (Howell et al., *Phytochemistry*, 66, 2281-2291 (2005)). More recently, Liu and coworkers proposed a mechanism for the PAC-mediated decrease of bacterial adhesion. Atomic force microscopy (AFM) studies showed that PACs induced a shortening of the P-fimbriae proteins, resulting in reduced adhesive forces between the bacterium and the AFM probe tip (Liu et al., *Biotechnol. Bioeng.*, 93, 297-305 (2006)).

In contrast to the nature of PACs' interaction with P-fimbriae proteins, the present findings point to several differences with respect to the nature of PACs' recognition of LPS. First, LPS binding is not specific to the A-type interflavan linkage. PACs from cranberries contain both A- and B-type interflavan subunit bonds while tea and grape PACs contain exclusively B-type interflavan linkages. Still, PACs from all three sources efficiently bound LPS. Second, data obtained for cranberry PACs demonstrated that larger polymers (fraction with a degree of polymerization of twenty-one) possess the highest degree of LPS binding activity. Finally, while other studies on the anti-bacterial adhesion properties of PACs have concentrated almost exclusively on PACs' effects on uropathogenic *E. coli*, the present data clearly shows that cranberry PACs bind LPS from multiple Gram-negative bacterial species. Further, binding studies showed that cranberry PACs recognize mutant LPS bearing shorter polysaccharide chains as well as diphosphoryl lipid A with an affinity comparable to that for native LPS. Thus, the lipid A moiety plays a predominant role in PACs' recognition of LPS.

The LPS binding activity of cranberry PACs' can have a significant impact on the interaction of LPS with LPS-responsive cells. In the current model of cellular interaction with LPS, LPS binding protein (LBP) present in serum binds to and presents LPS to the membrane-resident receptor CD14, which in turn transfers LPS to the bipartite receptor complex, TLR4/MD2 (Shimazu et al., *J. Exp. Med.* 189, 1777-1782 (1999)). MD2 is the LPS-binding unit of the receptor while TLR4 serves as the signal transduction component (Shimazu; Nagai et al., *Nat. Immunol.*, 3, 667-672 (2002); Schromm et al., *J. Exp. Med.*, 194, 79-88 (2001)). The TLR4/MD2-LPS complex ultimately undergoes endocytosis involving a caveolae-dependent uptake mechanism as part of LPS-induced receptor down-regulation (Shuto et al., *Biochem. Biophys. Res. Commun.*, 338, 1402-1409 (2005)). While debate currently exists as to whether TLR4 physically contacts LPS, it is clear that TLR4/MD2 and LPS form a stable complex on the cell surface and that LPS binding to MD2 is a prerequisite for TLR4 signaling activity (Visintin et al., *J. Immunol.*, 175, 6465-6472 (2005)) and LPS endocytosis (Husebye et al., *Embo. J.*, 25, 683-692 (2006); Shuto et al., *Biochem. Biophys. Res. Commun.*, 338, 1402-1409 (2005)).

In HEK 293 cells expressing the full complement of LPS receptors, it was found that cranberry PACs modestly reduced the binding of LPS to the cell surface while they significantly inhibited LPS endocytosis. In membrane binding experiments, cranberry PACs were slightly more potent at abrogating LPS interaction with the cell membrane than was diphosphoryl lipid A, a known MD2 receptor agonist and LPS antagonist (Muroi et al., *J. Biol. Chem.*, 281, 5484-5491 (2006)). PACs were less efficient than a CD14 function perturbing antibody at abrogating LPS binding. This is consistent with CD14's established role as the initial point of membrane interaction for LPS. An inhibitory effect of cranberry PACs on the endocytosis of LPS nearly equivalent to that of lipid A was noted in internalization assays. Based on these results and the known dependence of LPS endocytosis on efficient LPS interaction with MD2 (Shutto et al., *Biochem. Biophys. Res. Commun.*, 338, 1402-1409 (2005)), it can be reasoned that cranberry PACs played a predominant role in abrogating LPS interaction with the TLR4/MD2 receptor complex. Indeed, receptor binding studies showed that while PACs achieved a maximal 40% inhibition of LPS interaction with CD14, they completely inhibited LPS binding to TLR4/MD2 over the same concentration range. Further, PACs inhibited NF-κB activation in a manner that was not overcome by high LPS concentrations, even when present at a six-fold molar excess over PACs.

Other reports have described the inhibition of LPS-induced production of inflammatory cytokines by PACs. Bodet et al. demonstrated that a PAC-enriched fraction from cranberry juice concentrate inhibited the LPS-induced production of IL-6, IL-8, and prostaglandin E2 in gingival fibroblasts (Bodet et al., *Eur. J. Oral. Sci.*, 115, 64-70 (2007)) and TNFα and RANTES (Regulated on Activation Normal T-cell Expressed and Secreted) in macrophages (Bodet et al., *J. Dent. Res.*, 85, 235-239 (2006)). While this fraction was shown to inhibit the phosphorylation state of intracellular signaling proteins, the exact mechanism of the signaling inhibition was not elucidated. The present findings, however, point to a mechanism of LPS inhibition in which PACs bind directly to and neutralize LPS by blocking its interaction with TLR4/MD2. Further, in contrast to other LPS binding substances, this interaction with LPS is not readily overcome by excess concentrations of LPS. This has remained a shortcoming in the development of other LPS binding substances as therapeutic reagents for sepsis. The results suggest, therefore, that the multivalent nature of the PAC polymeric structure allows for other stabilizing interactions with the polysaccharide chain of LPS.

PACs are structurally quite different from other previously described LPS scavengers or LPS receptor antagonists such as polymyxin B or lipid A-like substances. Further, their LPS binding properties suggest that they may hold promise for the development of new therapies for the in vivo treatment of sepsis. At a minimum, their potent LPS binding activity, low cost, and widespread availability from natural sources should make them useful in biotechnology applications wherein the removal and purification of endotoxin is required.

Having described the invention, the following examples are given to illustrate specific applications of the invention. These specific examples are not intended to limit the scope of the invention described in this application.

EXAMPLE 1

Purification of Proanthocyanidins—Dialyzed cranberry juice concentrate (DCC) was produced from Mountain Sun pure unsweetened cranberry juice (100% strength, Celestial Group, Inc.) by dialysis against water (6,000 MWCO dialysis tubing) and filtration through a 0.2 µm filter. PACs (in which nonspecific polyphenols have been removed) were obtained from whole cranberry juice, Welch's 100% red grape juice, or Lipton black tea via purification by hydrophobic adsorption chromatography using a Sephadex LH20 column (Hagerman, "The tannin chemistry handbook" http://www.users.muohio.edu/hagermae/tannin.pdf (2002)). Whole juice was reduced by rotary evaporation to a minimum volume and resuspended to the original volume in 70% acetone, sonicated for 30 min, and filtered with Whatman #3 filter paper. Resuspension, sonication, and filtration of the insoluble material was repeated twice more and all liquid was combined. This solution was reduced by rotary evaporation to remove all acetone and resolubilized in 75% ethanol to twice the original volume. Tea was extracted by sonication of one family sized tea bag in 200 mL 70% acetone for 20 min (repeated 3 times). For each preparation, the solutions were combined, reduced by rotary evaporation, and resolubilized in 200 mL 75% ethanol. This solution was applied to a Sephadex LH20 column in batches equal to the bed volume. Small phenolics were removed by elution with ethanol equivalent to five times the bed volume. PACs were elated with acetone and reduced by rotary evaporation to a minimum volume. PACs recovered from whole cranberry juice were subsequently fractionated by differential dialysis against water containing 5% ethanol for further characterization. Fractions were collected as those which pass through 2,000 MWCO tubing (Spectra/Por; Dial<2k); those which pass through 3,500 MWCO tubing (Spectra/Por CE) but are retained by the 2,000 MWCO (Dial 2-3k); those that pass through 6,000 MWCO tubing (Spectra/Por Membrane MWCO 6-8000) but are retained by the 3,500 MWCO tubing (Dial 3-6k); and those which are retained by the 6,000 MWCO tubing (Dial 6k). All materials were dried to powder under a nitrogen stream for storage. Purified materials were dissolved in 33% ethanol/$H_2O$ for use in binding experiments. The degree of polymerization of each purified compound was determined by modified vanillin assay combined with the acid butanol assay PAC concentrations were determined by radial diffusion assay using tannic acid as a standard (Hagerman, "The tannin chemistry handbook" http://www.users.muohio.edu/hagemnae/tannin.pdf (2002); Hagerman, *J Chem Ecol.* 1987, 13 437) Analysis of purified materials by thiolysis and HPLC indicated no low molecular weight species remaining following LH20 separation (Hammerstone et al. *J. Nutr.* (2000) 130: 2086S-2092S; Gu et al., *J. Agric. Food Chem.* (2002) 50: 4852-4860; Prieur et al., *Phytochemistry* (1994) 36:781-784; Sun et al., *J. Agric. Food Chem.* (1998) 46:1390-1396). On the basis of these analyses, the PACs were considered to be devoid of sugars, acids, and low molecular weight contaminants.

TABLE 1

Proanthocyanidin Specifications

| PAC Source | Tannic Acid Equiv. (µM) (1 mg/mL) | Average Degree of Polymerization |
|---|---|---|
| Cranberries | 63.4 | 12.6 |
| Black Tea | 49.8 | 4.1 |
| Grape Juice | 29.9 | 7.2 |
| Cranberry Juice | 39.0 | 8.9 |
| Cranberries, Fraction 1 | 38.3 | 21.7 |

EXAMPLE 2

Non-specific Adhesion of *E. coli*—The Naval Research Laboratory Array Biosensor employs a protein-coated glass waveguide for the detection of analytes of interest (Rowe et al., *Anal. Chem.*, 71, 433 (1999); Taitt et al., *Microbial. Ecol.*, 47, 175 (2004); Golden et al., *Talanta*, 65, 1078 (2005)). The surface of the waveguide has a patterned array of capture molecules with non-specific passivating molecules used to coat other regions of the surface (Sapsford et al., *Anal. Chem.*, 74, 1061 (2002); Ngundi et al., *Anal. Chem.*, 77, 148 (2005); Shriver-Lake et al., *Anal. Chem.*, 67, 2431 (1995)). Fluorescence-based detection of targets is dependent on discrimination of capture molecule areas from other areas of the waveguide. Non-specific adhesion of targets to unexpected areas of the surface negatively impacts limits of detection as well as false positive/negative rates for the Array Biosensor.

Figure 1:
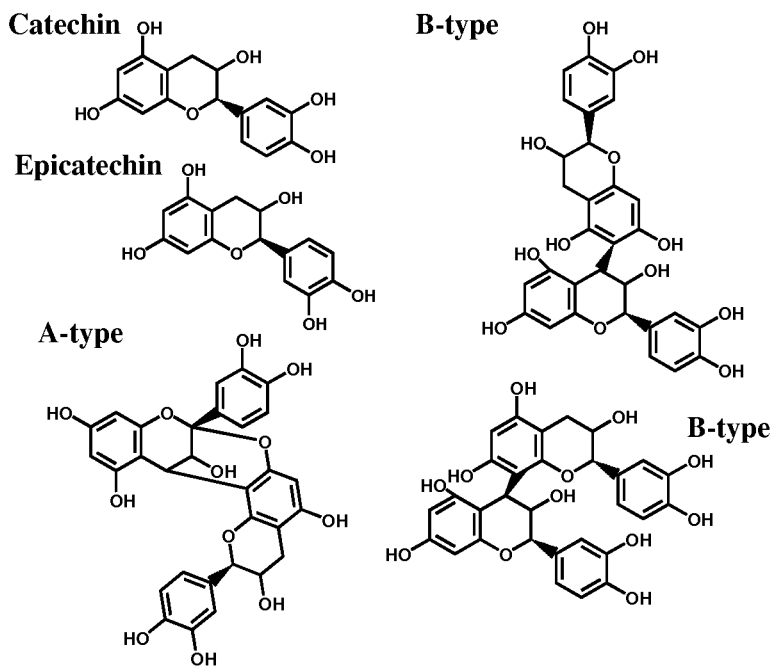
FIG. 1 shows further proanthocyanidin structure. PACs are composed of subunits such as catechin and epicatechin. B-Type PACs contain a single intermolecular bond either between carbons 4 and 8 or between carbons 4 and 6 while A-type PACs contain two intermolecular bonds between carbons 4 and 8 and carbon 2 and the oxygen of carbon 7 (Foo et al., *J Nat Prod.*, 63, 1225 (2000)).
Figure 2:
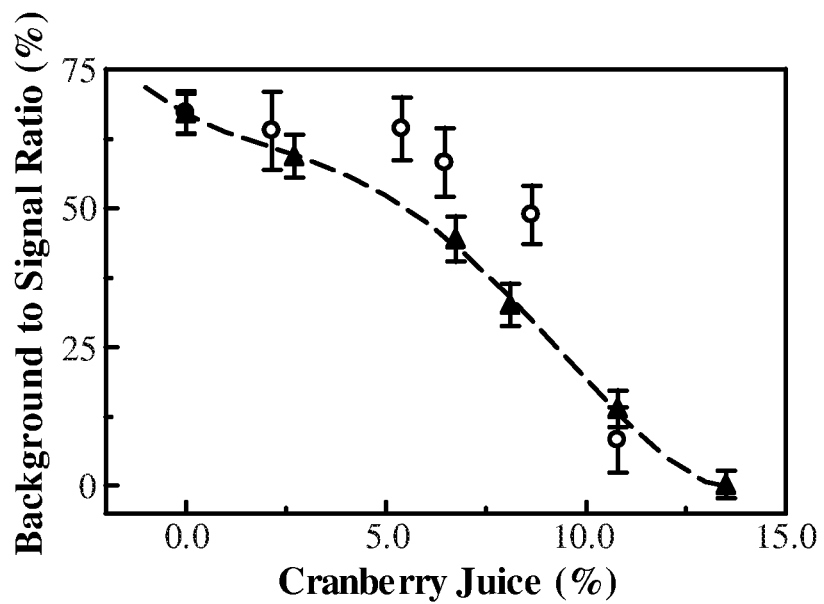
FIG. 2 shows the impact of cranberry juice on non-specific adhesion. The background intensity is expressed as the ratio of the mean background intensity to the mean fluorescence signal intensity. Spiking of bacterial samples with cranberry juice (▲) and dialyzed filtered cranberry juice (○) produces similar improvement in background signals.

The combination of a nonpathogenic *E. coli* strain (ATCC 35218) and a low affinity antibody (rabbit polycolonal antibody to *E. coli*; Abcam, Inc; Cambridge, Mass.) was found to produce a degree of nonspecific binding which made discrimination of signal from background intensities difficult (Johnson-White et al., *Anal. Chem.*, 78, 853 (2006)). Bacterial cells adhere through interactions involving surface proteins and/or lipopolysaccharide (LPS). Traditional approaches to reduction of nonspecific binding (for example blocking waveguide surfaces or spiking samples with proteins or sugars) were unsuccessful. Based on the impact of cranberry juice on bacterial cell adhesion in the urinary tract, the juice was investigated as a potential mediator of adhesion in the Array Biosensor. FIG. 2 presents data on the ratio of background intensity to signal intensity for samples assayed with varying concentrations of cranberry juice. Ocean Spray 100% Cranberry and Concord Grape juice blend containing 27% cranberry juice was used. In the absence of juice, background intensity was 67% of the total signal. Addition of 50% juice blend (equivalent to 13.5% cranberry juice) reduced the background intensity to less than 1% of the total signal (Johnson-White). Spiking samples with grape juice was not found to produce this effect on the background signal (Welch's Purple 100% Grape Juice). Spiking of samples with apple juice, orange juice, and even white cranberry juice (Ocean Spray 100% Juice Blend) also did not result in reduction of background signals. White cranberry juice is produced from cranberries harvested early before the red color and tart flavor are developed. The white cranberry juice blend used contains 13.5% cranberry juice. This difference in concentration was accounted for when samples were spiked so that concentrations similar to those used with the red cranberry juice were investigated.

Several mechanisms have been described for the inhibition of bacterial cell adhesion by cranberry juice (Steinberg et al., *J. Antimicrob. Chemoth.*, 54, 86 (2004); Brumfelt et al., *Lancet*, 1, 186 (1962); Klepser et al., *J. Infect. Dis. Pharmaco.*, 6, 1 (2003)). The acidity of the juice, the sugar content including the rare D-mannose component, and the presence of a rare polyphenolic component have been proposed as contributing factors. Controlling the pH of the juice spiked samples eliminated acidity as a causative factor. The sugar content of the juice was eliminated as a factor through spiking of *E. coli* samples with similar concentrations of fructose, glucose, and mannose. Waveguide surface passivation was also eliminated as a potential mechanism through studies of the impact of sample spiking on advancing contact angle. Though the contact angle was strongly impacted on clean glass slides when standard bacterial cell preparations were spiked, there was no noticeable impact on the protein coated slides used in the Array Biosensor. The interaction of *E. coli* with human epithelial cells in the urinary tract is inhibited by A-type proanthocyanidins from cranberry juice through interference with the p-fimbriae proteins on the bacterial cell surface (Liu et al., *Biotechnol. Bioeng.*, 93, 297 (2006); Howell et al., *Faseb J.*, 15, A284 (2001)). In order to investigate the potential impact of PACs on adhesion to the glass waveguides, sugars and other small molecules were eliminated from cranberry juice (Langer's Cranberry Concentrate) through dialysis against water (Spectra/Por Membrane MWCO 6-8000) ((Steinberg et al., *J. Antimicrob. Chemoth.*, 54, 86 (2004). Colloidal particles were removed through filtration of the dialyzed material using a 0.2 µm filter (Acrodisc PF; Gelman Sciences, Ann Arbor, Mich.). The dialyzed material was reconcentrated under nitrogen to a 27% cranberry juice equivalent and used to spike samples for Array Biosensor assays. This dialyzed filtered cranberry juice produced results similar to those observed when samples were spiked with the cranberry juice blend.

EXAMPLE 3

Figure 3:
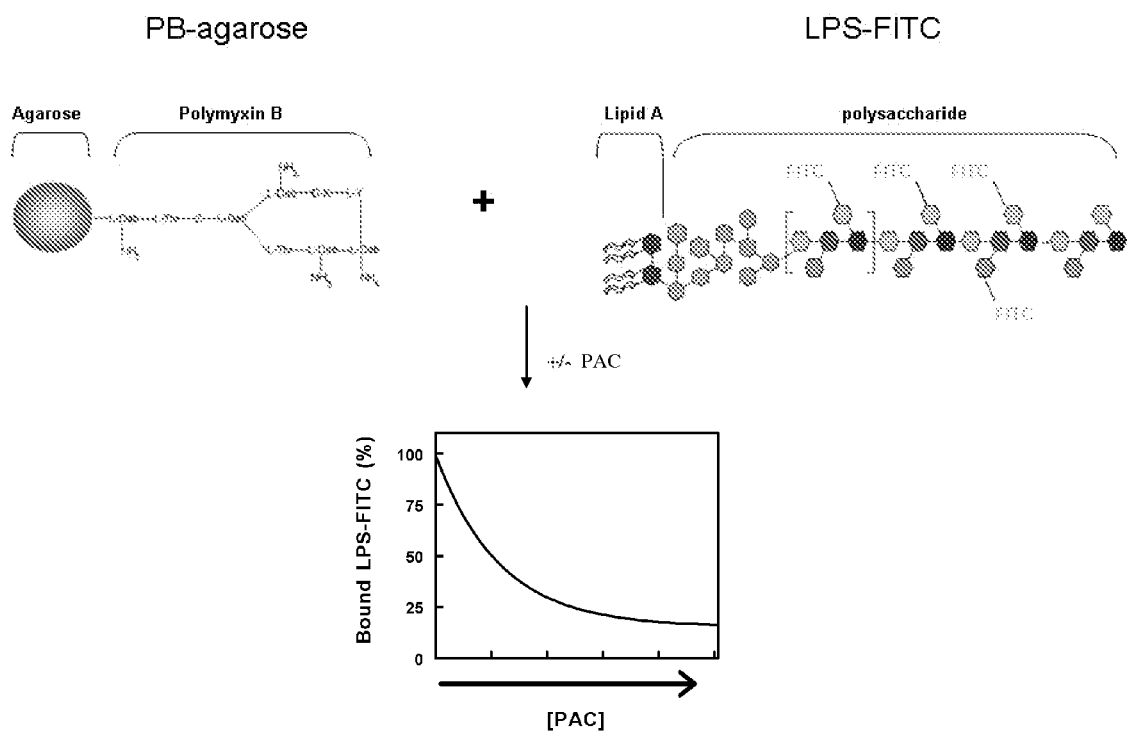
FIG. 3 shows a schematic representation of agarose-PB bead pull-down assay. PB immobilized onto agarose beads are incubated with fluorescein-labeled LPS. After centrifugation and washing, the amount of fluorescence associated with the beads is proportional to the amount of LPS bound to PB.
Figure 4:
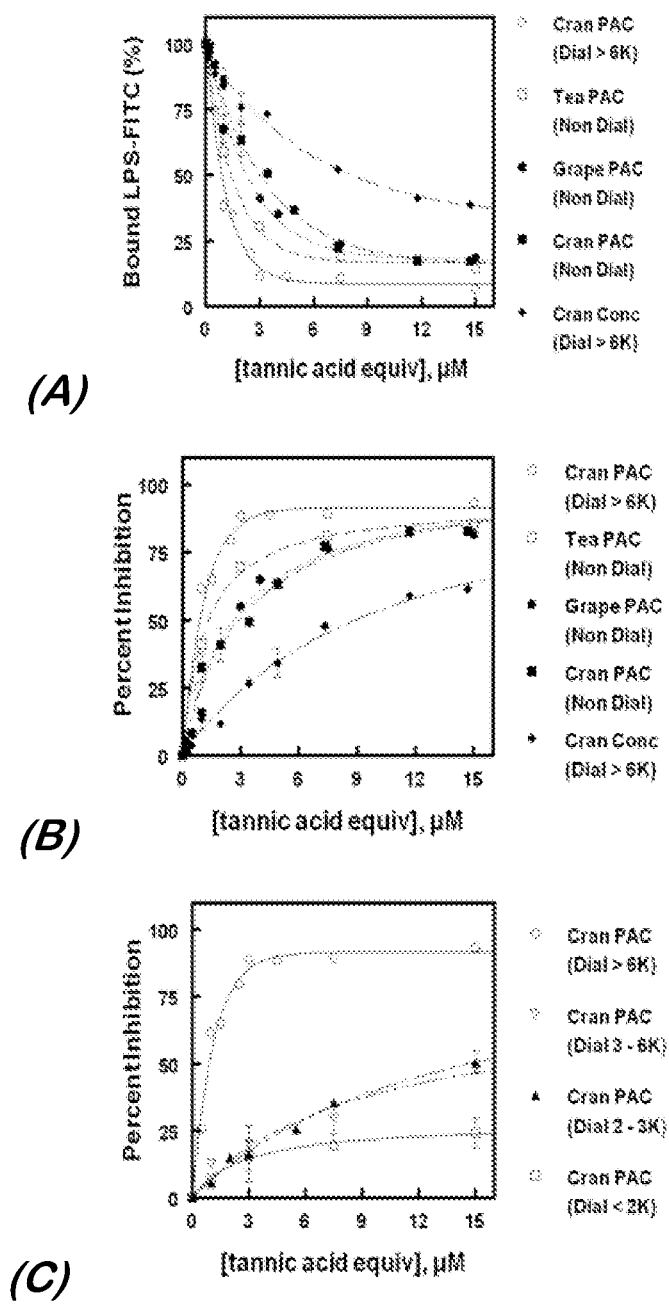
FIG. 4 shows the interaction of PACs with LPS. (A) The data shows the percentage of LPS bound to immobilized polymyxin B after co-incubation of LPS with PACs from cranberry, tea, and grapes. The LPS-binding activity of PACs from all three sources was concentration-dependent. (B) The data in (A) are presented as percent inhibition. (C) For cranberry PACs, the majority of the LPS-binding activity was contained within the fraction composed of polymers retained by 6,000 MWCO dialysis membranes (average degree of polymerization of 21). Data in A-C are the mean±standard deviation and are representative of triplicate experiments. PAC concentrations are reported in tannic acid equivalents.

LPS binding assays—The ability of both of PACs to inhibit the interaction of LPS with PB was assessed using an agarose bead-based pull-down assay (FIGS. 3, 4). Polymyxin B (10 µM, conjugated to agarose beads (Sigma)) was incubated with 100 nM LPS-FITC (*E. coli* serotype B5:055, Sigma) in the absence or presence of DCC, non-dialysed LH20 PAC, or size-fractionated LH20 PAC in a final volume of 250 µL 0.05 M Tris buffer (pH 8.5). Reactions were stirred for 1 h at 25° C. in the dark. Unbound LPS-FITC was removed by three rounds of centrifugation and washing with 250 µL of 0.05 M Tris buffer, followed by resuspension in 200 µL of nuclease free water. Serial dilutions of each sample were prepared in nuclease free water and the fluorescence was measured by excitation at 495±2.5 nm and emission at 535±2.5 nm using a Saphire fluorescence plate reader (Tecan, Durham, N.C.). Comparable experiments were performed with LPS from *Salmonella, Shigella*, and *Pseudomonas* and LPS from mutant strains of *Salmonella minnesota* (Rc mutant) and *E. coli* EH 100 (Ra mutant). The latter two strains contain polysaccharide chains of varying lengths relative to native LPS. Binding experiments were also performed with diphosphoryl lipid A. Conjugation of lipid A and LPS was performed with fluorescein isothiocyanate (Sigma) per the manufacturer's instructions and materials were subjected to dialysis against PBS for separation from unbound dye. In all cases, the degree of conjugation was determined by spectroscopy to be approximately 2-3 fluoresceins per mole of labeled species.

Using a solid-phase binding assay, the ability of both A- and B-type PACs to bind LPS was assessed by determining their ability to inhibit the interaction of *E. coli* LPS with immobilized polymyxin B. Binding experiments comparing PACs from cranberries (which possess both A- and B-type linkages) to those from tea and grapes (which possess exclusively B-type linkages) demonstrated that PACs bearing both linkages bound efficiently to LPS in a dose-dependent manner (FIG. 4(A)). When these data were plotted as percent inhibition, cranberry PACs that had been enriched through dialysis to contain polymers of larger molecular weight exhibited the most potent LPS binding activity with an $IC_{50}$ of 0.7 µM (FIG. 4(B)). PACs from tea (non-dialyzed) were the next most active with an $IC_{50}$ of 1.1 µM. Non-dialyzed PACs from grapes and cranberries exhibited comparable relative affinities for LPS ($IC_{50}$=3.0 µM). Dialyzed cranberry concentrate (not enriched for PACs) exhibited the lowest relative affinity for LPS ($IC_{50}$=10.5 µM). When the LPS binding activities of cranberry PACs produced by differential dialysis were compared, a positive correlation between the relative affinity for LPS and PAC molecular weight was observed. Indeed, the larger molecular weight polymers exhibited higher LPS binding activity relative to the lower molecular weight PACs (FIG. 4(C)). Thus, all subsequent experiments were performed using the PAC fraction from cranberries with an average degree of polymerization of twenty-one (heretofore referred to as "cranberry PACs").

The LPS binding activity of cranberry PACs was not limited to *E. coli* LPS as evidenced by their ability to bind with comparable affinities to LPS from *Salmonella, Shigella*, and *Pseudomonas*. Further, cranberry PACs bound to two LPS mutants bearing shorter polysaccharide chains of varying lengths (an Ra mutant from *E. coli* and an Rc mutant from *Salmonella*) with only a three-fold lower affinity relative to wild-type LPS. These results are summarized in Table 2.

TABLE 2

Binding of cranberry LH20 PAC[a] to LPS and Lipid A

| Bacterial species | Apparent $IC_{50}$ (µM)[b] - LPS | Apparent $IC_{50}$ (µM)[b] - Lipid A[c] |
|---|---|---|
| *Escherichia coli* | 0.7 ± 0.2 | 0.3 ± 0.1 |
| *Salmonella minn.* | 1.2 ± 0.3 | |
| *Shigella flexneri* | 1.6 ± 0.3 | |
| *Escherichia coli* EH 100 (Ra mutant) | 2.1 ± 0.7 | |
| *Salmonella minn.* (Rc mutant) | 2.1 ± 0.5 | |
| *Pseudomonas aeruginosa* | 3.4 ± 1.1 | |

[a]Corresponds to PACs of greater than 6,000 molecular weight.
[b]Apparent $IC_{50}$s are shown with their corresponding 90% confidence intervals.
[c]Diphosphoryl form of lipid A As polymyxin B is known to bind to the lipid A portion of LPS (David et al., *Biochim. Biophys. Acta.*, 1165, 147-152 (1992)), it was reasoned that interaction with the lipid A moiety plays a predominant role in cranberry PACs' recognition of LPS. Indeed, cranberry PACs efficiently inhibited the binding of *E. coli* lipid A to polymyxin B with an apparent $IC_{50}$ of 0.3 µM, a relative affinity that is only two-fold greater than its affinity for intact *E. coli* LPS (Table 2). This result confirms the importance of the lipid A moiety in cranberry PACs' binding to LPS.

EXAMPLE 4

Analysis of LPS membrane binding and endocytosis. Human embryonic kidney cells (HEK 293) stably expressing human CD14 and TLR4/MD2 (HEK-CD14-TLR4/MD2; Invivogen) were grown in chambered wells and incubated with 25 nM LPS (*E. coli* serotype O55:B5, Sigma) in the absence or presence of 0.5 µM LH20 PAC (Dial>6K) for 1.5 h at 37° C. In control experiments, TLR4 or CD14 was functionally blocked by co-incubation with an anti-TLR4 or anti-CD14 monoclonal antibody (500 nM in binding sites, Abeam, Inc.) or lipid A (Sigma). After incubation, the cells were washed with PBS (10 min) twice and either fixed (with 3.7% paraformaldehyde) to assess LPS membrane binding or fixed and permeabilized (with 0.1% Triton X-100) to determine LPS internalization. After blocking with 1% normal goat serum, membrane bound or internalized LPS was detected using a goat anti-LPS antibody (O/K serotype-specific, Abcam) conjugated to fluorescein. Nuclei were counter-stained with DAPI. Imaging was performed using an Olympus IX-71 microscope. The relative amounts of membrane-associated or intracellular fluorescence were quantified by image analysis using Image J software (NIH, v. 1.37). Data is reported as the mean channel fluorescence from membrane-associated or internalized LPS and represents the analysis of 10 to 20 cells from each sample (minimum 10 measurements per each cell). Merged images were produced using Photoshop CS2 (ver. 9).

Figure 5:
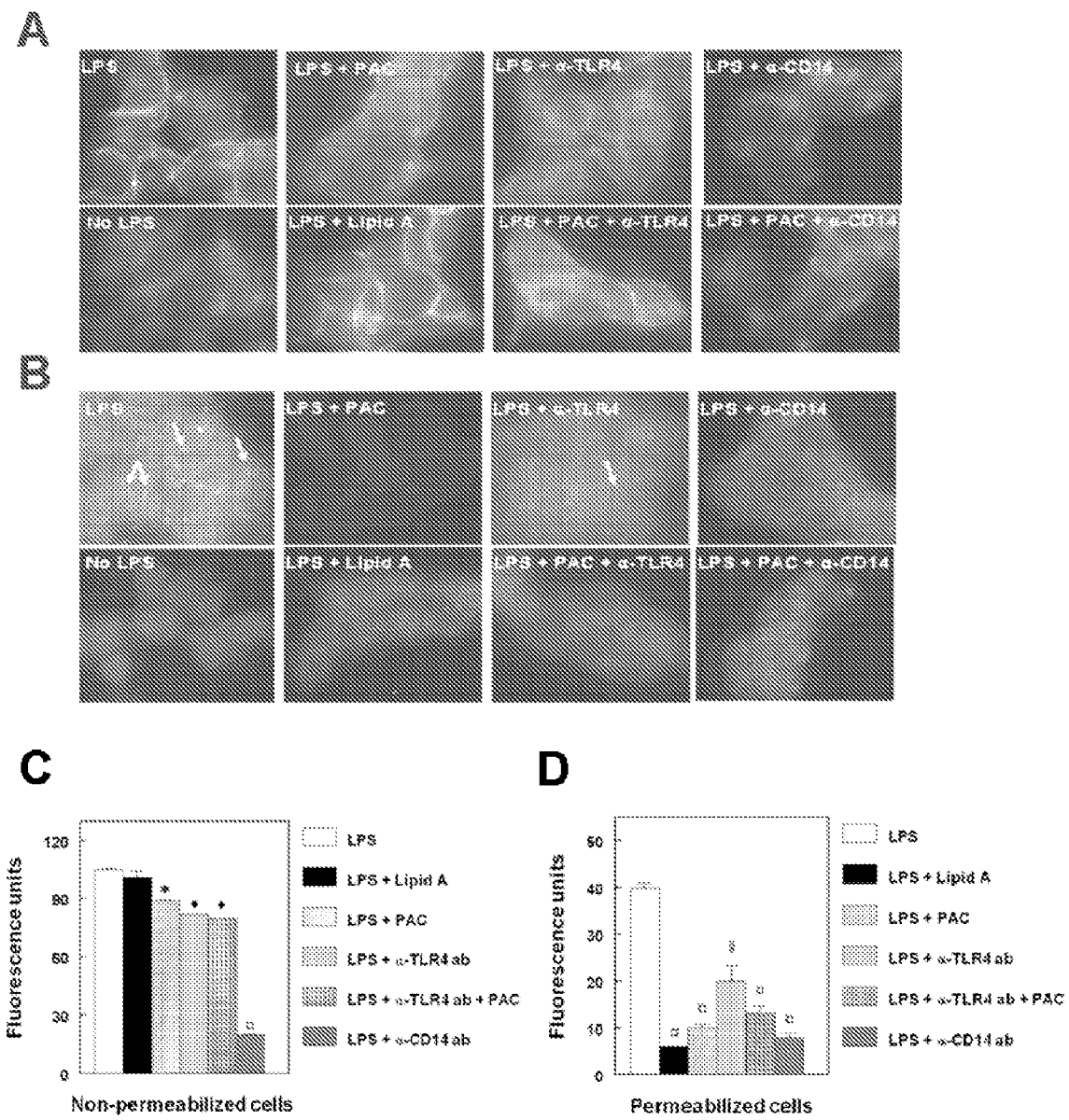
Figure 6A:
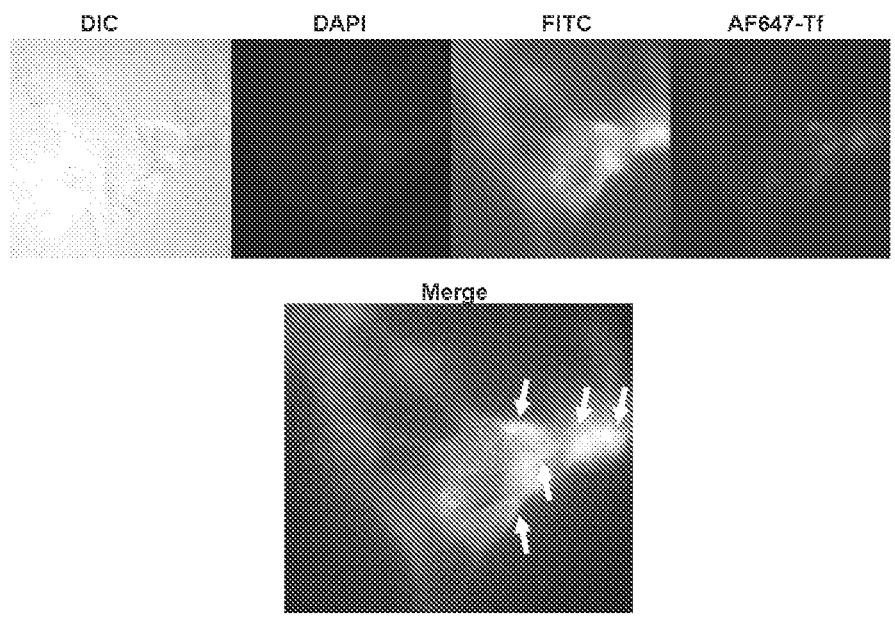
FIG. 6 shows that cranberry PACs inhibit endocytosis of LPS but do not inhibit overall endocytosis. Cellular binding assays were performed as described in FIG. 2 in the manuscript except an Alexa Fluor 647-labeled transferrin was added to the culture medium to label the endosomal compartment. After fixation and permeabilization of the cells, LPS was detected with a goat anti-LPS antibody conjugated to fluorescein. The data show that in the absence of PAC (panel A), the endocytosed LPS colocalizes largely with transferrin (indicated by arrows in the merged image). In the presence of PAC (panel B), however, LPS is largely present at the plasma membrane (indicating an inhibition of LPS endocytosis by PAC). The transferrin staining of the endosomal compartment, however, is similar to that seen in the absence of PAC. Thus, PAC inhibits LPS endocytosis but not overall endocytosis.
Figure 6B:
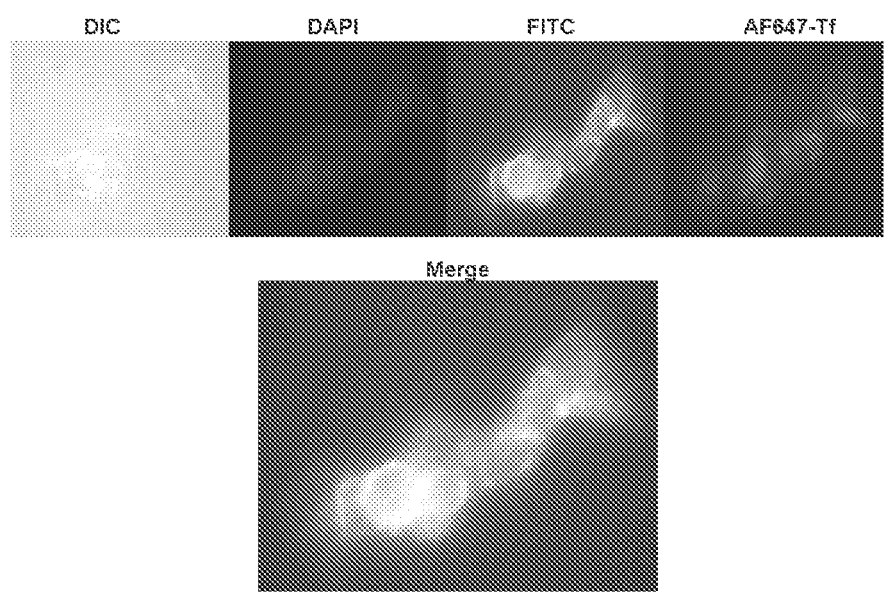

PACs Slightly Inhibit Membrane Binding of LPS and Significantly Inhibit LPS Endocytosis. Beyond the mere binding of LPS, a desirable attribute of LPS-binding compounds is the ability to inhibit LPS interaction with LPS-responsive mammalian cells. Based on their potent LPS-binding activity, it was reasoned that cranberry PACs could potentially inhibit LPS interaction with cells expressing the full complement of LPS receptors. Cellular binding studies performed in HEK 293 cells expressing CD14 and Toll-like receptor 4/MD2 (HEK-CD14-TLR4/MD2), revealed a distinct staining pattern corresponding to membrane-bound LPS (FIG. 5(A), frame "LPS") with minimal nonspecific binding (FIG. 5(A), frame "No LPS"). While co-incubation of LPS with lipid A did not significantly reduce LPS membrane binding, the presence of cranberry PAC resulted in a modest but significant decrease (~15%) in the amount of membrane-bound LPS (FIG. 5(C)). An anti-TLR4 function-perturbing antibody also caused a modest decrease in LPS binding (~23%), while this same antibody in combination with cranberry PAC did not impart any further LPS binding perturbation. It was found that an anti-CD14 function-perturbing antibody mediated the largest degree of LPS binding inhibition (~84% inhibition), demonstrating the highly important role of CD14 in LPS membrane binding. Analysis of LPS internalization demonstrated that lipid A and cranberry PAC significantly inhibited endocytosis of LPS (FIG. 5(B)) with degrees of inhibition of 84% and 76%, respectively (FIG. 5(D)). The anti-TLR4 antibody mediated ~50% inhibition of LPS endocytosis while co-incubation of the antibody with cranberry PAC increased this inhibition further to ~62%. The anti-CD14 antibody mediated approximately 80% inhibition of LPS endocytosis. In control experiments, the addition of Alexa Fluor 647-labeled transferrin, a marker of the endocytotic pathway, to the culture medium containing PACs and LPS showed that PACs had no inhibitory effect on normal endocytosis as a robust staining of the endosomal compartment was observed in both the presence and absence of PACs. Thus, PACs specifically inhibited the endocytosis of LPS while having no inhibitory effect on overall endocytosis (FIG. 6).

In the current model of cellular interaction with LPS, LPS-binding protein (LBP) present in serum binds to and presents LPS to the membrane-resident receptor CD14, which in turn transfers LPS to the bipartite receptor complex, TLR4/MD2 (Shimazu et al., *J. Exp. Med.,* 1999, 189, 1777-1782). MD2 is the LPS-binding unit of the receptor while TLR4 serves as the signal transduction component (Shimazu; Nagai et al., *Nat. Immunol.,* 2002, 3, 667-672; Schromm et al., *J. Exp. Med.,* 2001, 194, 79-88). The TLR4/MD2-LPS complex ultimately undergoes endocytosis involving a caveolae-dependent uptake mechanism as part of LPS-induced receptor down-regulation (Shuto et al., *Biochem. Bioph. Res. Co.,* 2005, 338, 1402-1409). While debate currently exists as to whether TLR4 physically contacts LPS, it is clear that TLR4/MD2 and LPS form a stable complex on the cell surface and that LPS binding to MD2 is a prerequisite for TLR4 signaling activity (Visintin et al., *J. Immunol.,* 2005, 175, 6465-6472) and LPS endocytosis (Shuto; Husebye et al., *EMBO J.,* 2006, 25, 683-692). It was hypothesized, therefore, that cranberry PACs inhibit LPS endocytosis by inhibiting LPS interaction with the TLR4/MD2 complex.

PAC Inhibition of LPS binding to LBP, CD14 and TLR4/MD2. Human CD14 (Cell Sciences) was adsorbed onto ELISA plates in PBS overnight at 4° C. Histidine-tagged-human TLR4/MD2 (R&D Systems) or human LPS-binding protein (LBP, Biometec) was captured overnight at 4° C. onto ELISA plates prepared by the passive adsorption of anti-polyhistidine monoclonal antibody (R&D Systems). Wells were blocked for 30 min at 37° C. with 1% normal goat serum in PBS. Binding of 5 nM *E. coli* LPS-FITC was performed for 30 min at 37° C. in 1% fetal bovine serum in PBS in the presence or absence of LH20 PAC. Soluble CD14, when present, was at a final concentration of 25 nM. Bound LPS-FITC was detected using a goat anti-fluorescein-horseradish peroxidase conjugate (Abcam) and tetra-methylbenzidine substrate (Kierkegaard and Perry). In the absence of serum, binding of LPS-FITC to CD14 or to TLR4/MD2 was below the detection limit.

Figure 7:
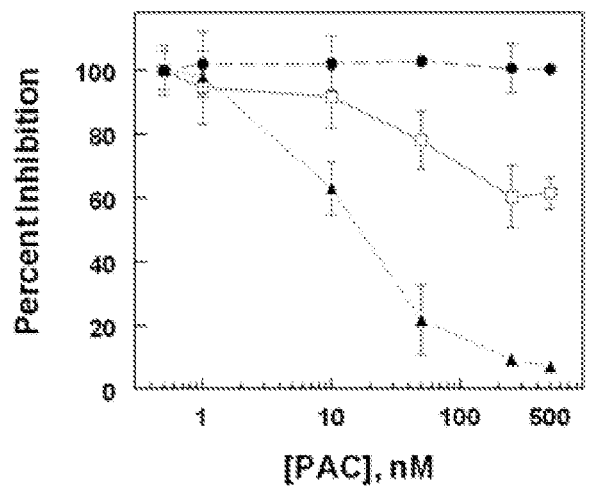
FIG. 7 shows that cranberry PACs inhibit LPS interaction with CD14 and TLR4/MD2 but not with LBP. (A) PACs completely inhibit binding of *E. coli* LPS to immobilized TLR4/MD2 (solid triangles) and partially inhibit binding of LPS-FITC to immobilized CD14 (open squares). No inhibition of LPS:LBP interaction was noted (solid circles). (B) PACs inhibit both the direct and CD14-mediated binding of LPS-FITC to TLR4/MD2. In the presence of 25 nM CD14, the binding of LPS to immobilized TLR4/MD2 is enhanced approximately 4-fold (open triangles) relative to when soluble CD14 is absent (solid triangles). The inset shows both data sets plotted as percent of control. In both instances, the degrees of inhibition to immobilized TLR4/MD2 are comparable. Data are the mean±standard deviation of two representative experiments.
Figure 7:
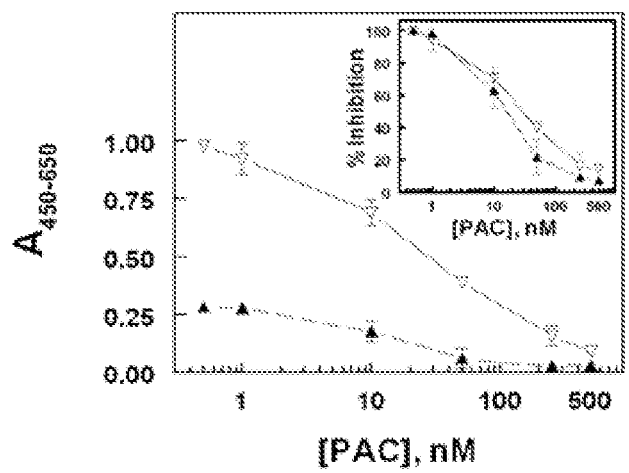

PACs Abrogate LPS Interaction with CD14 and TLR4/MD2 bit not LPS-Binding Protein (LBP). Binding studies were performed in order to address the effect of cranberry PACs on LPS interaction with its cognate receptors. FIG. 7(A) shows the results of binding experiments conducted to measure the ability of cranberry PACs to inhibit the binding of *E. coli* LPS to immobilized LBP, CD14, or TLR4/MD2. It was apparent that cranberry PACs had no significant effect on LPS interaction with LBP while they achieved a maximum inhibition of 38% of LPS binding to CD14 at the highest PAC concentration tested (500 nM). Over the same concentration range, cranberry PACs completely inhibited LPS interaction with TLR4/MD2, with an $IC_{50}$ of 20 nM PAC. It was further found that in the presence of soluble CD14, the amount of LPS bound by TLR4/MD2 was increased approximately four-fold (FIG. 7(B)), consistent with the established role of CD14 in mediating the transfer of LPS to TLR4/MD2 (Aderem et al., *Nature,* 2000, 406, 782-787; Medzhitov, *Nat. Rev. Immunol.,* 2001, 1, 135-145). The degree to which cranberry PAC inhibited LPS binding to TLR4/MD2, however, remained unchanged demonstrating the ability of PACs to inhibit the CD14-mediated transfer of LPS to immobilized TLR4/MD2 (FIG. 7(B), inset).

Quantification of NF-κB activation. HEK-CD14-TLR4/MD2 cells were transiently transfected with the NF-κB-inducible reporter plasmid, pNiFty2-SEAP (Invivogen), which encodes secreted embryonic alkaline phosphatase (SEAP) under the control of a 5×NF-κB-inducible promoter. Cells were seeded into wells of a 96-well plate ($4 \times 10^4$ cells/well) and transfected using Effectene reagent (Qiagen) per manufacturer's instructions. After 48 h, the cells were stimulated for 16 h with 2 nM LPS in the presence or absence of cranberry PACs. SEAP activity was measured in tissue culture supernatants using a calorimetric SEAP assay kit (Invivogen) according to the manufacturer's protocol.

Figure 8:
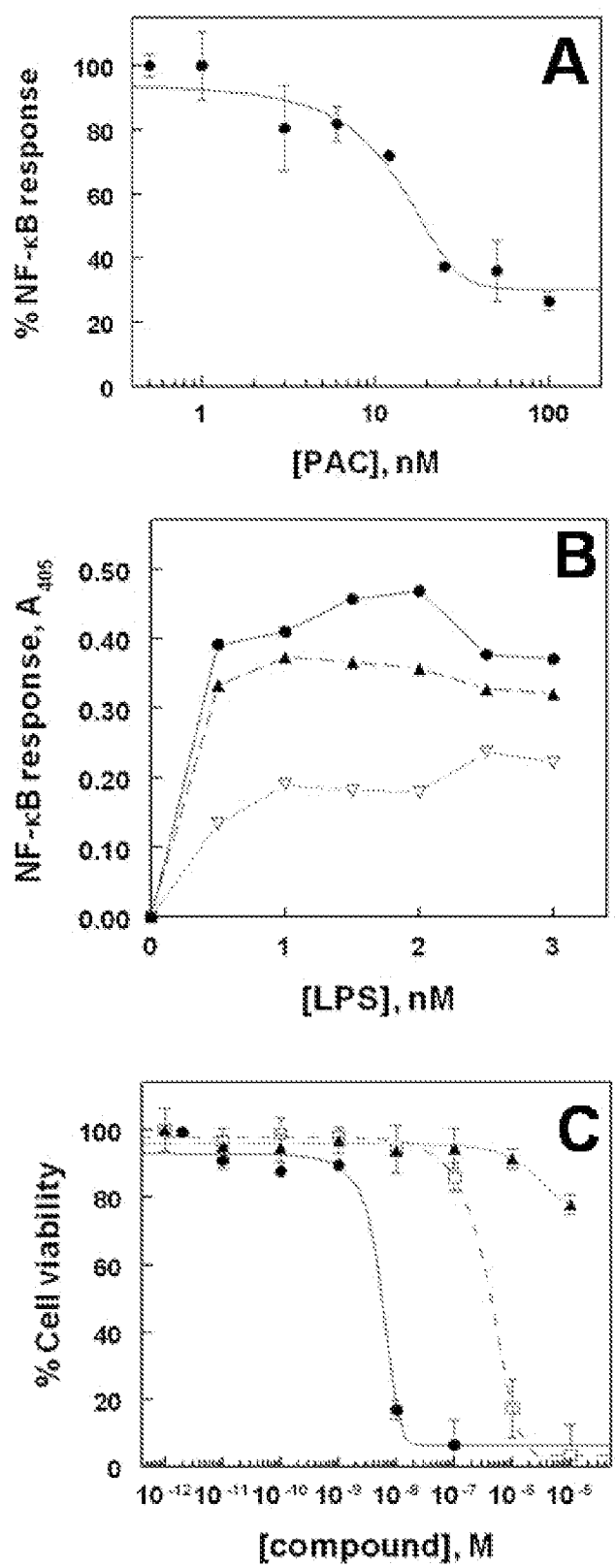
FIG. 8 shows the inhibition of NF-κB activation by and cytotoxicity of PACs in LPS-responsive HEK 293 cells. (A) Cranberry PACs inhibit LPS-induced NF-κB activation in a dose-dependent manner. (B) The inhibitory effect of PACs is not overcome by excess LPS. HEK-CD14-TLR4/MD2 cells were stimulated with LPS at the indicated concentrations in the presence of cranberry PAC at the following concentrations: 0 nM (solid circles), 0.5 nM (solid triangles), or 10 nM (open triangles). (C) PACs are not toxic to LPS-responsive cells over the same concentration range at which they inhibit NF-κB activation and PACs are ~100-fold less toxic than LPS.

PACs Inhibit LPS-induced NF-κB Activation. Based on the LPS-binding activity of cranberry PACs and their abrogation of LPS interaction with cell surface receptors, it was reasoned that PACs could also inhibit the LPS-induced activation of the transcription factor, NF-κB. NF-κB activation by LPS leads to the expression of proinflammatory cytokines, resulting in the metabolic and physiologic changes that ultimately lead to pathological conditions, including sepsis (Baeuerle et al., *Ann. Rev. Immunol.,* 1994, 12, 141-179). As shown in FIG. 8(A), cranberry PACs inhibited the activation of NF-κB in a dose-dependent manner in HEK-CD14-TL4/MD2 cells stimulated with 2 nM LPS, with an $IC_{50}$ of 25 nM PAC. Further, the data in FIG. 8(B) show that this inhibition was not readily overcome by an excess of LPS. In the absence of cranberry PAC, an increase in LPS resulted in a corresponding increase in the NF-κB response. When the LPS concentration was increased above 2 nM, a slight decrease in the response was noted, due primarily to LPS-induced cytotoxicity (see below). In the presence of 0.5 nM cranberry PAC, a consistent decrease in the NF-κB response was observed across all LPS concentrations. Even when LPS was present at 3 nM (a six-fold molar excess over PAC), NF-κB activation was not restored to control levels. When cranberry PAC was present at 10 nM, a consistent decrease in the NF-κB response (approximately 50% across all LPS concentrations) was observed relative to the control.

EXAMPLE 5

Cytotoxicity assays—Cellular toxicity was measured using a calorimetric cell proliferation assay (CellTiter96™, Promega). HEK-CD14-TLR4/MD2 cells were seeded into the wells of a 96-well plate ($1\times10^4$ cells/well) and cultured with a dose range of test compounds for 48 h prior to assay according to the manufacturer's instructions. Examination of PACs' cytotoxicity revealed an $IC_{50}$ for toxicity of 700 nM, with no toxic effects observed at concentrations below 100 nM (FIG. 8(C)). When compared to LPS ($IC_{50}$ for toxicity of 6 nM), PACs were more than 100-fold less toxic. In comparison to native LPS, the diphosphoryl form of lipid A did not elicit toxicity at concentrations below 3 μM.

EXAMPLE 6

Immobilization of PACs and LPS binding assay—To determine the ability of PAC materials to effectively bind bacteria and bacterial cell components upon immobilization to a solid support, PACs from cranberry and grape juices were covalently attached to the surface of a glass microscope slide (waveguide) using a modification of a common technique used for protein immobilization (Rowe et al., *Anal. Chem.*, 71, 3846 (1999)). Catechin monomer and buffer only areas were also included as controls. Briefly, the waveguides, glass microscope slides (Daigger, Wheeling, Ill.), were cleaned by immersion in potassium hydroxide/methanol solution (Cras et al., *Biosens. Bioelectron.*, 14, 683 (1999)) followed by rinsing and drying. The clean waveguides were then incubated with 2% (3-mercaptopropyl)triethoxysilane (Pierce Chemicals, Rockford, Ill.) in toluene for 45 minutes followed by rinsing and drying. The slides were immersed in 1.8 mM N-[p-maleimidophenyl]isocyanate (PMPI) in ethanol for 1 hour. The maleimide-group of PMPI reacts with the sulfhydryl-group provided by the silane reaction leaving the isocyanate-group free to react with the hydroxyl-groups of PACs. Following PMPI immobilization, waveguides were rinsed with deionized water, dried, and mounted in PDMS patterning templates described previously (Rowe). Solutions of 10 mg/mL PACs from cranberry or grape juices, catechin in 10 mM PBS with 10% methanol, and PBS with 10% methanol (negative control) were incubated in the lanes of the PDMS template overnight at 4° C. Patterning solutions were flushed from the PDMS lanes using PBS and the slides were rinsed with deionized water, dried, and stored at 4° C. until use. The ability of the immobilized PACs to bind LPS was investigated using a stationary assay. PDMS flow cells with channels were affixed perpendicularly to those of the patterning template so that each of the sample lanes was exposed to each of the patterned rows. Sample lanes were rinsed with PBS followed by injection of various concentrations of LPS-FITC (*E. coli* O55:B5, Sigma) in PBS. The LPS-FITC was incubated in the lanes for 1 hour, followed by rinsing with PBS and deionized water. Slides were imaged using evanescent wave fluorescence spectroscopy with excitation at 496 nm and emission collected above 515 nm. Upon exposure to a concentration range of LPS-FITC, it was apparent that PACs from cranberry and grape juices bound specifically to LPS-FITC while the catechin and buffer controls show no binding even at the highest concentrations tested. Thus, PACs retain their ability to bind LPS upon immobilization to a solid support.

EXAMPLE 7

PAC and catechin immobilization—Purified PACs and catechin (Sigma-Aldrich) were immobilized onto activated thiol-Sepharose® 4B (Sigma-Aldrich) via a (N-[p-maleimidophenyl]isocyanate) (PMPI; Pierce) crosslinker. Sepharose® was swelled in deionized water for 1 hour (1 g dry material in 15 mL $H_2O$). The material was then washed using fresh dI-$H_2O$ over five suspend/centrifuge/decant cycles (total 50 mL per gram dry starting material). Suspension was accomplished using a vortex and centrifuge steps were conducted at 3,000 g for five minutes. The Sepharose® material (total volume 5 mL per gram starting material) was then rinsed three times with ethanol (total volume 30 mL per gram starting material). The PMPI crosslinker was incubated with the rinsed Sepharose material for 1 hour at room temperature under constant agitation using a 10-fold molar excess of PMPI over the thiol-group concentration with 3% dimethylsulfoxide in ethanol (10 mL per gram starting material). Incubation was followed by centrifuging, decanting, and rinsing in 50% ethanol for three cycles. The Sepharose was then incubated overnight at 4° C. in ethanol with PAC or catechin using a 10-fold molar excess of analyte in 50% ethanol (10 mL per gram starting material). As a final step, the Sepharose was rinsed over four cycles using 50% ethanol (40 mL total per gram starting material) and resuspended in 0.02% sodium azide in $H_2O$ (16 mL final volume per gram starting material). The materials were stored in the dark at 4° C. until use. PAC concentrations for bead sets were determined by Prussian blue assay.

EXAMPLE 8

Fluorescence-based pull down assays for lipopolysaccharide (LPS) were conducted in 50 mM TRIS at pH 8.0 using Sepharose-immobilized PACs and agarose-immobilized polymyxin B (Sigma-Aldrich, St. Louis, Mo.). Immobilized capture molecules and LPS were incubated at room temperature for 1 hour with constant agitation followed by rinsing and transfer to a 96-well plate. The fluorescence of the FITC-labeled LPS (from *E. coli* O55:B5; Sigma-Aldrich) was measured using a Tecan XSafire monochrometer-based micro plate reader at 495 nm excitation and 520 nm emission (5 nm bandwidths).

Figure 9:
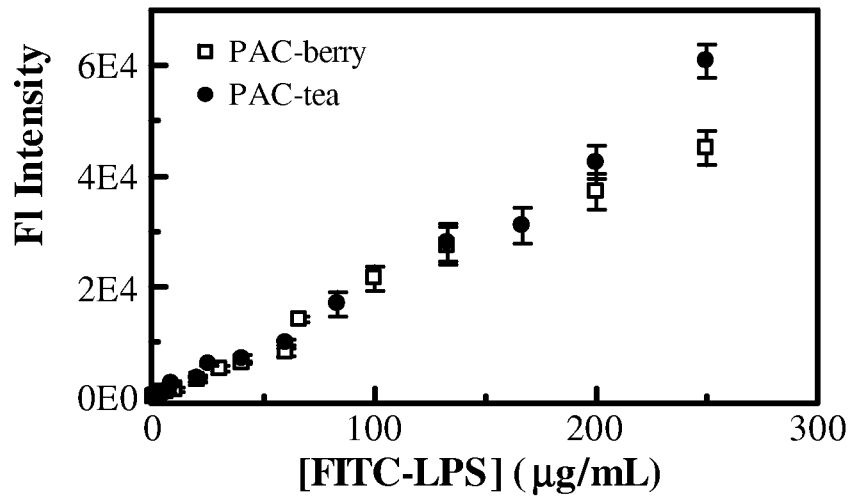
FIG. 9 shows the capture of FITC-LPS by immobilized proanthocyanidins. Sepharose-immobilized PACs from cranberries (open squares) and tea (solid circles) bind LPS in solution as indicated by the increase in fluorescence intensity in the pull down assay. The capture molecule concentration is 5.5 µM for PACs from tea and 6.0 µM for PACs from cranberries

PAC beads for use in pull-down assays were generated by immobilizing proanthocyanidins from cranberries, cranberry juice, tea, and grape juice onto Sepharose beads. An additional bead set was generated by immobilizing the fraction of PACs from cranberries with molecular weights greater than 6,000 onto Sepharose beads. Assays conducted using these beads demonstrated that all five bead sets could be used to bind FITC-labeled LPS from solution (50 mM TRIS pH 8). Concentration dependence curves for beads with immobilized PACs from tea and cranberries are presented in FIG. 9. Beads coated with catechin were used to verify a low degree of nonspecific binding of FITC-LPS to the Sepharose and crosslinker. In order to further verify that binding of LPS to the Sepharose beads was via a specific interaction with the immobilized PAC, a competitive assay was used in which soluble PAC was added to the sample solution during the assay. Increasing the concentration of soluble PAC was found to decrease the fluorescence intensity resulting from the pull-down assay as expected (FIG. 10).

Figure 10:
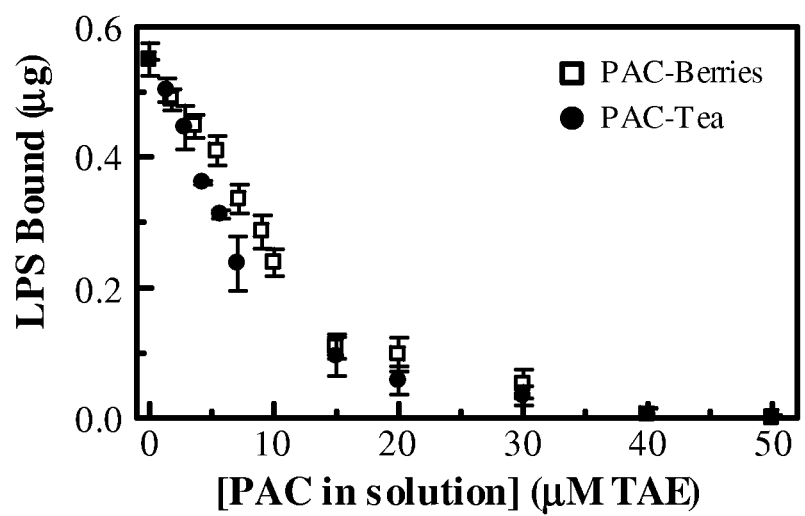
FIG. 10 shows the impact of soluble PAC presence on the immobilized PAC capture of LPS from solution. A. The presence of PACs in solution inhibits the binding of LPS to Sepharose beads as indicated by the decrease in fluorescence intensity upon increasing the PAC concentration. FITC-LPS concentration was 71 µg/mL and capture molecule concentration was 5.5 µM for PACs from tea (solid circles) and 6.0 µM for PACs from cranberries (open squares).

In FIG. 10 soluble PACs from tea have been added to assays conducted with immobilized PACs from tea while soluble PACs from cranberries have been added to assays conducted with immobilized PACs from cranberries. Inhibition of 50% of LPS binding by the PAC-tea beads occurs at 6.5 µM while 50% inhibition of binding by PACs from cranberries occurs at 9.8 µM. Capture molecule concentration in the two assay types is 5.5 µM for PAC-tea beads and 6.0 µM for PAC-cranberry beads. The discrepancies between the capture molecule concentration and the level at which 50% inhibition occurs are likely due to several considerations. Capture molecule concentrations have been estimated using the Prussian blue assay as compared to the Prussian blue assay conducted on soluble PACs from the same source. This assignment assumes that all components of the immobilized polyphenolics are accessible in a manner similar to those in solution. The analysis also assumes that all degrees of polymerization were immobilized equally so that the degree of polymerization achieved on the Sepharose was similar to that observed in solution. Though relatively low soluble PAC concentrations were not found to quench the fluorescence of FITC-LPS, immobilized PACs represent a locally high concentration. The impact can be seen in FIG. 9. The increase in fluorescence intensity with increasing target concentration cannot be described by a simple model. In addition, although PAC absorbance in the wavelength range of interest is low with molar extinction coefficients on the order of 10,000, the locally high concentration of PACs reduces the excitation intensity available to the FITC-LPS. All of these factors may contribute to either an actual difference, as with the Prussian blue assay, or to an observed difference, as with the quenching, in the expected concentration of soluble PACs needed to obtain 50% inhibition of LPS binding by the immobilized PACs.

Figure 11:
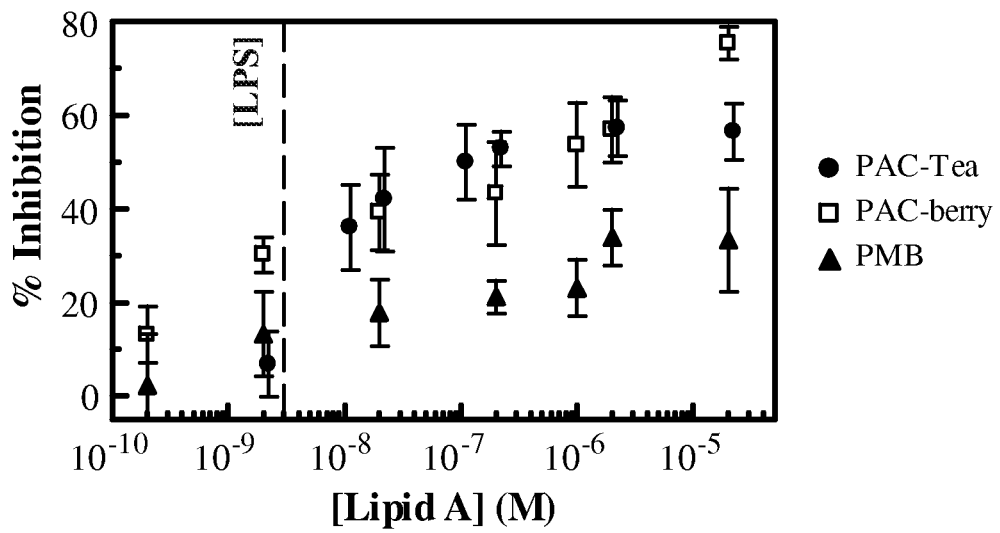
FIG. 11 shows the impact of soluble lipid A presence on the capture of LPS by immobilized PACs. Addition of Lipid A to PAC beads prior to completion of pull-down assays for the presence of FITC-LPS results in a decrease in the fluorescence intensity obtained. FITC-LPS concentration was 71

Though inhibition of the PMB-LPS interaction (Example 3) indicated the interaction of PACs with LPS in a manner which prevented PMB binding, it did not guarantee the interaction of PACs with the lipid A portion of LPS. To further investigate this potential interaction, an assay for the presence of FITC-LPS using PAC-beads was conducted after equilibration of the PAC beads with varying concentrations of lipid A (FIG. 11). Assays were conducted with 3 µg/mL FITC-LPS (approx. 3 nM). The presence of lipid A was found to inhibit FITC-LPS binding by immobilized PACs with $IC_{50}$ values of 100 nM and 500 nM for PACs from tea and cranberries, respectively. The addition of lipid A concentrations as high as 100 µM, however, failed to result in inhibition of greater than 80% of the FITC-LPS binding. It is unclear whether this is a result of the unavailability of lipid A, which may form micelles or precipitate at the higher concentrations, or of the fact that binding interactions between LPS and the immobilized PACs are not limited to the lipid A portion of LPS.

In order to evaluate the utility of Sepharose-immobilized proanthocyanidins for LPS capture, a side-by-side comparison was made to that of commercially available agarose-immobilized polymyxin B. FIG. 12 presents the percent LPS captured as a function of the concentration of capture molecule for PMB and PACs from tea and cranberries. Quenching of the FITC-LPS fluorescence intensity when bound to the immobilized PAC presented a difficulty in direct comparison of the capture materials. This issue was addressed by measuring the fluorescence intensity of the FITC-LPS remaining in solution after incubation with the capture material. Percent captured values are based on comparison of the fluorescence remaining after incubation with capture material to an identically handled sample which contained no capture molecule. Both types of PAC beads performed slightly better than the PMB beads. This was expected based on the inhibition of polymyxin B binding of LPS (Example 3) by the proanthocyanidins.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A composition comprising:
   a plurality of proanthocyanidin compounds having more than one degree of polymerization;
      wherein the average degree of polymerization of all the proanthocyanidins in the composition is from 20 to 22; and
      wherein the composition comprises a proanthocyanidin compound containing at least one A-type linkage.

2. The composition of claim 1, wherein the proanthocyanidin consists of catechin and epicatechin units.

3. A method comprising:
   administering to an immunosuppressed patient or a patient diagnosed with sepsis or septic shock a composition comprising a plurality of proanthocyanidin compounds having more than one degree of polymerization and containing at least one A-type linkage;
      wherein the average degree of polymerization of all the proanthocyanidins in the composition is from 20 to 22.

4. The method of claim 3, wherein the proanthocyanidin consists of catechin and epicatechin units.

5. The method of claim 3, wherein the proanthocyanidin is administered in a combination therapy with an antibiotic, a chemotherapeutic, a radionucleide, an immunosuppressive drug, a plasmapheresis treatment, or a combination thereof.

6. The method of claim 3, wherein the proanthocyanidin is conjugated to an antibiotic, a chemotherapeutic, a radionucleide, or an immunosuppressive drug.

7. A method comprising:
   administering to a patient diagnosed with a gram negative bacterial infection a composition comprising a plurality of proanthocyanidin compounds having more than one degree of polymerization and containing at least one A-type linkage;
      wherein the average degree of polymerization of all the proanthocyanidins in the composition is from 20 to 22.

8. The method of claim 7, wherein the proanthocyanidin consists of catechin and epicatechin units.

9. The method of claim 7, wherein the proanthocyanidin is administered in a combination therapy with an antibiotic, a chemotherapeutic, a radionucleide, an immunosuppressive drug, a plasmapheresis treatment, or a combination thereof.

10. The method of claim 7, wherein the proanthocyanidin is conjugated to an antibiotic, a chemotherapeutic, a radionucleide, or an immunosuppressive drug.

* * * * *